US011045418B2

(12) United States Patent
Hefesha et al.

(10) Patent No.: US 11,045,418 B2
(45) Date of Patent: Jun. 29, 2021

(54) LIPID PARTICLE FORMULATIONS FOR DELIVERY OF RNA AND WATER-SOLUBLE THERAPEUTICALLY EFFECTIVE COMPOUNDS TO A TARGET CELL

(71) Applicants: BioNTech RNA Pharmaceuticals GmbH, Mainz (DE); Tron-Translationale Onkologie an der Universitatsmedizin der Johannes Gutenberg-Universitat Mainz GGmbH, Mainz (DE)

(72) Inventors: Hossam Hefesha, Wiesbaden (DE); Ugur Sahin, Mainz (DE); Heinrich Haas, Mainz (DE); Sebastian Kreiter, Mainz (DE); Yves Hüsemann, Wiesbaden (DE); Mustafa Diken, Mainz (DE); Kerstin Walzer, Darmstadt (DE)

(73) Assignees: BioNTech RNA Pharmaceuticals GmbH, Mainz (DE); Tron-Translationale Onkologie an der Universitatsmedizin der Johannes Gutenberg-Universitat Mainz, Mainz (DE)

( * ) Notice: Subject to any disclaimer, the term of this patent is extended or adjusted under 35 U.S.C. 154(b) by 4 days.

(21) Appl. No.: 15/554,132

(22) PCT Filed: Mar. 30, 2016

(86) PCT No.: PCT/EP2016/056920
§ 371 (c)(1),
(2) Date: Aug. 28, 2017

(87) PCT Pub. No.: WO2016/156398
PCT Pub. Date: Oct. 6, 2016

(65) Prior Publication Data
US 2018/0263907 A1 Sep. 20, 2018

(30) Foreign Application Priority Data

Mar. 31, 2015 (WO) ................. PCT/EP2015/057118

(51) Int. Cl.
| | | |
|---|---|---|
| *A61K 9/107* | (2006.01) | |
| *A61K 9/127* | (2006.01) | |
| *A61K 48/00* | (2006.01) | |
| *A61K 31/675* | (2006.01) | |
| *A61K 31/7105* | (2006.01) | |
| *A61K 9/00* | (2006.01) | |
| *A61K 31/663* | (2006.01) | |
| *A61K 45/06* | (2006.01) | |
| *A61K 39/395* | (2006.01) | |
| *A61P 35/00* | (2006.01) | |
| *A61K 39/00* | (2006.01) | |
| *A61K 47/18* | (2017.01) | |
| *A61K 47/24* | (2006.01) | |

(52) U.S. Cl.
CPC .......... *A61K 9/1075* (2013.01); *A61K 9/0019* (2013.01); *A61K 9/1272* (2013.01); *A61K 31/663* (2013.01); *A61K 31/675* (2013.01); *A61K 31/7105* (2013.01); *A61K 39/0011* (2013.01); *A61K 39/395* (2013.01); *A61K 45/06* (2013.01); *A61K 47/186* (2013.01); *A61K 47/24* (2013.01); *A61K 48/00* (2013.01); *A61P 35/00* (2018.01); *A61K 2039/54* (2013.01)

(58) Field of Classification Search
CPC ................................................... A61K 9/1075
See application file for complete search history.

(56) References Cited

U.S. PATENT DOCUMENTS

2011/0236345 A1* 9/2011 Sampson ........... A61K 39/0011
424/85.2

FOREIGN PATENT DOCUMENTS

| JP | 2011-526923 | 10/2011 |
|---|---|---|
| JP | 2015-514076 | 5/2015 |
| JP | 2016-537304 | 12/2016 |
| WO | WO 2005/044280 | 5/2005 |
| WO | WO 2013/143683 | 10/2013 |
| WO | WO 2015/043613 | 4/2015 |

OTHER PUBLICATIONS

Phua et al. (Nanoscale. Jul. 21, 2014; 6(14): 7715-7729) (Year: 2014).*
Chen et al. (International Journal of Nanomedicine. 2013; 8: 137-145). (Year: 2013).*
Perche et al. (Nanomedicine: Nanotechnology, Biology, and Medicine 7 (2011) 445-453). (Year: 2011).*
Mendonca et al., "Co-encapsulation of anti-BCR-ABL si RNA and imatinib mesylate in transferrin receptor-targeted sterically stabilized liposomes for chronic myeloid leukemia treatment," Biotechnology and Bioengineering, vol. 107, No. 5, Dec. 1, 2010, pp. 884-893.

(Continued)

*Primary Examiner* — Scott Long
(74) *Attorney, Agent, or Firm* — McDonnell Boehnen Hulbert & Berghoff LLP

(57) ABSTRACT

The present invention relates to lipid particles comprising at least one cationic lipid, at least one water-soluble therapeutically effective compound and RNA. Further, the present invention relates to a pharmaceutical composition comprising such particles. Said pharmaceutical composition is useful for inducing an immune response. It is also useful in a prophylactic and/or therapeutic treatment of a disease involving an antigen. Furthermore, the present invention relates to a method for producing the particles.

8 Claims, 16 Drawing Sheets

(56) References Cited

OTHER PUBLICATIONS

Yan et al., "Codelivery of zoledronic acid and double-stranded RNA from core-shell nanoparticles," International Journal of Nanomedicine, vol. 8, No. 1, Jan. 3, 2013.
Salzano et al., "Self-assembly nanoparticles for the delivery of bisphosphonates into tumors," International Journal of Pharmaceutics, Elsevier BV, NL, vol. 403, No. 1-2, Jan. 17, 2011, pp. 292-297.
Dileo et al., "Lipid-Protamine-DNA-Mediated Antigen Delivery to Antigen-Presenting Cells Results in Enhanced Anti-tumor Immune Responses," Mol Ther. 7(5):640-48 (May 2003).
Hess et al., "Vaccination with mRNAs encoding tumor-associated antigens and granulocyte-macrophage colony-stimulating factor efficiently primes CTL responses, but is insufficient to overcome tolerance to a model tumor/self antigen," Cancer Immunol Immunother. 55(6):672-83 (Jun. 2006; Epub Aug. 20, 2005).
Regelin et al., "Biophysical and lipofection studies of DOTAP analogs" Biochimica et Biophysica Acta 1464:151-64 (2000).
Su et al., "In vitro and in vivo mRNA delivery using lipid-enveloped pH-responsive polymer nanoparticles," Mol Pharm. 8(3):774-87 (Jun. 2011; Epub Apr. 1, 2011).
Weissman et al., "HIV Gag mRNA Transfection of Dendritic Cells (DC) Delivers Encoded Antigen to MHC Class I and II Molecules, Causes DC Maturation, and Induces a Potent Human In Vitro Primary Immune Response," The Journal of Immunology, 165:4710-17 (2000).

\* cited by examiner

DOTMA/DOPE/ZA/RNA

LIPID PARTICLE FORMULATIONS FOR DELIVERY OF RNA AND WATER-SOLUBLE THERAPEUTICALLY EFFECTIVE COMPOUNDS TO A TARGET CELL

REFERENCE TO RELATED APPLICATION(S)

This application is a U.S. national phase application under 37 USC 371 of International Patent Application no. PCT/EP2016/056920, filed Mar. 30, 2016, which claims the benefit of priority of International Application No. PCT/EP2015/057118, filed Mar. 31, 2015.

TECHNICAL FIELD OF THE INVENTION

The present invention relates to lipid particles comprising RNA and one or more therapeutically effective compounds and pharmaceutical compositions comprising such particles for delivery of both the RNA and the therapeutically effective compound(s) to a target organ or a target cell after parenteral administration. In more detail, the particles comprise RNA lipoplexes comprising at least one cationic lipid and RNA and one or more water-soluble therapeutically effective compound(s), such as (a) bisphosphonate(s). The RNA and the therapeutically effective compound(s) are taken up by the cell, the RNA is preferably translated into a peptide or protein and the therapeutically effective compound(s) exhibit(s) its physiological activity. The pharmaceutical composition of the invention is applicable for inducing or enhancing an immune response. It is also useful in a prophylactic and/or therapeutic treatment of a disease involving an antigen such as a protein. Furthermore, the present invention relates to a method for producing said lipid particles comprising RNA and one or more therapeutically effective compounds.

BACKGROUND OF THE INVENTION

The development of injectable pharmaceutical formulations for delivery of pharmaceutically active compounds is an unmet need with various therapeutic applications like treatment of cancer or other severe diseases. For such purpose, different types of nanoparticle formulations have been developed for drug delivery. Typically, the carrier particle is optimized according to the molecular properties of the drug to be delivered.

A typical uptake mechanism for nanoparticle formulations is endocytosis where the ingested particle is first enclosed in the endosome. For therapeutic applications it is often necessary that the cargo is released from the endosome into the cytosol. Major hurdles in pharmaceutical development of drug delivery formulations for water soluble compounds are undesired release of the cargo prior to cellular uptake as well as inefficient release from the endosomal lumen to the cytosol.

Delivery of certain water-soluble compounds can be achieved by using vesicular lipid vesicles which provide save transportation to the target site by fully encapsulating the active molecule. Such vesicular carriers must be sufficiently stable in order to avoid premature release of the cargo and to support cellular intake of the integral vesicle. Therefore, fluid-like lipids as commonly used for transfection are not suitable for such purpose.

It is also known in the art that DNA and RNA may be delivered by so-called lipoplex formulations, in which the DNA or RNA is bound to cationic lipids or liposomes to form injectable nanoparticle formulations.

The requirements of the described systems for delivery of both nucleic acids with substantial molecular weight and small water-soluble molecules tend to exclude each other. For delivery of small water-soluble molecules, vesicular carriers such as liposomes or capsules are preferred since they are sufficiently stable to prevent undesired release. However, such vesicular carriers are not ideally suited for the carriage of biological polyelectrolytes with moderate or high molecular weight such as RNA or DNA because the encapsulation efficacy is often low and electrostatic interactions of the nucleic acids with the lipid membrane of the carrier particle may evoke defects such as gaps and holes which expedite leakiness and the premature release of the encapsulated small molecules. Thus, the different molecular properties of low molecular weight water-soluble compounds and nucleic acids are detrimental to a joint drug delivery of both molecules. Furthermore, the drug delivery formulation should allow translation of the delivered DNA/RNA into protein.

Thus, there is a need of providing improved formulations for the delivery of therapeutically effective small molecules and nucleic acids to a target cell. Furthermore, such formulations should enable subsequent translation of the contained nucleic acid into the peptide or protein it codes for.

The inventors surprisingly found that the lipid particles described herein fulfill all of the above mentioned requirements.

SUMMARY OF THE INVENTION

In a first aspect, the present invention relates to a lipid particle comprising:
(i) at least one cationic and/or pH responsive lipid,
(ii) at least one water-soluble therapeutically effective compound, and
(iii) RNA.

In one embodiment, the lipid forms a structure receiving the at least one water soluble therapeutically effective compound and the RNA.

In one embodiment, the particle of the invention comprises a lamellar internal organization. In one embodiment, the lamellar internal organization comprises 2 to 40, preferably 2 to 20, more preferably 2 to 10, in particular 3 to 8 lamellae per row.

In one embodiment, the RNA is pharmaceutically active or encodes at least one pharmaceutically active peptide or protein such as an immunologically active peptide or protein. In one embodiment, the RNA encodes at least one antigen. In one embodiment, the antigen is a disease-associated antigen or elicits an immune response against a disease-associated antigen or cells expressing a disease-associated antigen.

In one embodiment, the therapeutically effective compound has a molecular mass lower than 1000 Da. In one embodiment, the therapeutically effective compound is useful in immunotherapy. In one embodiment, the therapeutically effective compound is an agent stimulating γδ T cells, preferably Vγ9Vδ2 T cells. In one embodiment, the agent stimulating γδ T cells is a bisphosphonate, preferably a nitrogen-containing bisphosphonate (aminobisphosphonate). In one embodiment, the agent stimulating γδ T cells is selected from the group consisting of zoledronic acid, clodronic acid, ibandronic acid, pamidronic acid, risedronic acid, minodronic acid, olpadronic acid, alendronic acid, incadronic acid and salts thereof.

In one embodiment, the particle of the invention comprises at least one helper lipid. In one embodiment, the helper lipid is a neutral lipid or negatively charged lipid. In one embodiment, the at least one helper lipid comprises 1,2-di-(9Z-octadecenoyl)-sn-glycero-3-phosphoethanolamine (DOPE), cholesterol (Chol), 1-palmitoyl-2-oleoyl-sn-glycero-3phosphocholin (POPC) and/or 1,2-dioleoyl-sn-glycero-3-phosphocholine (DOPC), preferably DOPC, DOPE and/or Chol.

In one embodiment, the at least one cationic lipid comprises 1,2-dimyristoyl-sn-glycero-3-ethylphosphocholine (DMEPC), 1,2-di-O-octadecenyl-3-trimethylammonium propane (DOTMA) and/or 1,2-dioleoyl-3-trimethylammonium propane (DOTAP), preferably DOTAP and/or DOTMA.

In one embodiment, the particle of the invention has an average diameter in the range of from about 50 nm to about 1000 nm. In one embodiment the particle has an average diameter in the range of from about 300 nm to about 800 nm. In one embodiment the particle has an average diameter of about 200 nm or less. Particles having an average diameter in the range of from about 300 nm to about 800 ran are preferably useful for targeting antigen presenting cells, preferably antigen presenting cells in the spleen, preferably professional antigen presenting cells such as dendritic cells. Particles having an average diameter of about 200 nm or less are preferably useful for targeting tumor cells.

In one embodiment, the particle has an average diameter
(i) smaller than 200 nm, or
(ii) in the range of from about 200 nm to about 1000 nm, preferably from about 200 nm to about 800 nm, more preferably from about 300 nm to about 600 nm.

In one embodiment the particle of the invention has a negative zeta potential.

In one embodiment, the particle of the invention is obtainable by addition of the RNA to a colloidal lipid dispersion comprising the at least one cationic lipid and the at least one water-soluble therapeutically effective compound. In one embodiment, the colloidal lipid dispersion comprising the at least one cationic lipid and the at least one water-soluble therapeutically effective compound is obtainable by injection of a solution of lipids (comprising the at least one cationic lipid) in at least one water-miscible organic solvent such as an ethanol solution of the lipids into an aqueous phase comprising the at least one water-soluble therapeutically effective compound.

In a second aspect, the present invention relates to a pharmaceutical composition comprising particles according to the first aspect.

In one embodiment, after systemic administration of the particles, at least a portion of the RNA and at least a portion of the therapeutically effective compound are delivered to a target cell, preferably to the same target cell. In one embodiment, at least a portion of the RNA and at least a portion of the therapeutically effective compound are delivered to the cytosol of the target cell. In one embodiment, the RNA is RNA encoding a peptide or protein and the RNA is translated by the target cell to produce the peptide or protein. In one embodiment, the target cell is a spleen cell, preferably an antigen presenting cell, more preferably a professional antigen presenting cell, more preferably a dendritic cell. Thus, particles of the invention may be used for delivering RNA and a therapeutically effective compound to such target cell. Accordingly, the present invention also relates to a method for delivering RNA and a therapeutically effective compound to a target cell, preferably to the same target cell, in a subject comprising the systemic administration of the particles of the invention comprising the RNA and the therapeutically effective compound to the subject. In one embodiment, the RNA and the therapeutically effective compound are delivered to the cytosol of the target cell. In one embodiment, the RNA is RNA encoding a peptide or protein and the RNA is translated by the target cell to produce the peptide or protein. In one embodiment, the target cell is a spleen cell, preferably an antigen presenting cell, more preferably a professional antigen presenting cell, more preferably a dendritic cell.

In one embodiment, after systemic administration of the particles, RNA accumulation and/or RNA expression in the spleen occurs. Thus, particles of the invention may be used for expressing RNA in the spleen.

In one embodiment, after systemic administration of the particles, no or essentially no RNA accumulation and/or RNA expression in the lung and/or liver occurs.

In one embodiment, after systemic administration of the particles, RNA accumulation and/or RNA expression in the spleen is at least 5-fold the amount of RNA accumulation and/or RNA expression in the lung and/or liver.

In one embodiment, after systemic administration of the particles, RNA accumulation and/or RNA expression in antigen presenting cells, preferably professional antigen presenting cells in the spleen occurs. Thus, particles of the invention may be used for expressing RNA in such antigen presenting cells.

In one embodiment, the antigen presenting cells are dendritic cells and/or macrophages.

In one embodiment, systemic administration is by parenteral administration, preferably by intravenous administration, subcutaneous administration, intradermal administration or intraarterial administration.

In one embodiment, the pharmaceutical composition further comprises one or more pharmaceutically acceptable carriers, diluents and/or excipients. In one embodiment, the pharmaceutical composition farther comprises at least one adjuvant.

In one embodiment, the pharmaceutical composition is formulated for systemic administration.

In a third aspect, the present invention relates to particles of the first aspect or a pharmaceutical composition of the second aspect for inducing or enhancing an immune response, preferably an immune response against cancer.

In a fourth aspect, the present invention relates to particles of the first aspect or a pharmaceutical composition of the second aspect for use in a prophylactic and/or therapeutic treatment of a disease involving an antigen, preferably a cancer disease.

In a fifth aspect, the present invention relates to a method for delivering an antigen to antigen presenting cells, preferably professional antigen presenting cells, in the spleen, or expressing an antigen in antigen presenting cells, preferably professional antigen presenting cells, in the spleen comprising administering to a subject particles of the first aspect or a pharmaceutical composition of the second aspect. In this aspect, the antigen or a portion thereof is preferably encoded by the RNA in the particles of the invention.

In one embodiment, the antigen presenting cells are dendritic cells and/or macrophages.

In a sixth aspect, the present invention relates to a method for inducing or enhancing an immune response, preferably an immune response against cancer, in a subject comprising administering to the subject particles of the first aspect or a pharmaceutical composition of the second aspect.

In a seventh aspect, the present invention relates to a method for stimulating, priming and/or expanding T cells in a subject comprising administering to the subject particles of the first aspect or a pharmaceutical composition of the second aspect.

In an eighth aspect, the present invention relates to a method of treating or preventing a disease involving an antigen, preferably a cancer disease, in a subject comprising administering to the subject particles of the first aspect or a pharmaceutical composition of the second aspect. In this aspect, the antigen or a portion thereof is preferably encoded by the RNA in the particles.

In a ninth aspect, the present invention relates to a method of producing a particle of the first aspect comprising the following steps of:
(i) providing a colloidal lipid dispersion comprising at least one cationic lipid and at least one water-soluble therapeutically effective compound, and
(ii) adding RNA to the lipid dispersion comprising at least one cationic lipid and at least one water-soluble therapeutically effective compound. In one embodiment, the method comprises dialyzing the colloidal lipid dispersion.

In one embodiment, the colloidal lipid dispersion comprising at least one cationic lipid and at least one water-soluble therapeutically effective compound is provided by injection of a solution of lipids (comprising at least one cationic lipid) in at least one water-miscible organic solvent such as an ethanol solution of lipids into an aqueous phase comprising the at least one water-soluble therapeutically effective compound.

In one embodiment, the number of positive charges derived from the cationic lipids divided by the number of negative charges derived from the RNA is between 0.025 and 4.

Embodiments of the cationic lipid, the therapeutically effective compound, the RNA and/or the particle produced are as described above.

In one even more preferred embodiment, the number of positive charges derived from the cationic lipids divided by the number of negative charges derived from the RNA is between 0.025 and 4, preferably is 0.025, 0.125, 0.250, 0.375, 0.500, 0.625, 0.750, 0.875, 1, 2, 3, or 4. This summary of the invention does not necessarily describe all features of the invention.

BRIEF DESCRIPTION OF THE FIGURES

FIG. 1 shows the retention of zoledronic acid (ZA) as a function of initial ZA concentration in colloidal lipid dispersions. The molar DOTMA/DOPE ratio in the used lipid composition was 66.66/33.33 (=2/1). ZA was dissolved in 100 mM HEPES buffer at concentration of 20 mg/ml and the pH adjusted to 4 approx. with NaOH. The lipid concentration was approx. 12 mM. Encapsulated and free zoledronic acid was quantified by HPLC. As can be seen, ZA retention raises steadily with increasing initial concentrations of ZA up to 4 mg/ml.

FIG. 2 shows the retention of zoledronic acid (ZA) as a function of DOTMA concentration in colloidal lipid dispersions. Colloidal lipid dispersions comprising ZA with different total molar fractions of lipid composition were prepared. The tested colloidal lipid dispersion composition contained DOTMA/DOPE in a 2/1 molar ratio and containing 3, 6, or 12 mM DOTMA, respectively. ZA was dissolved in 100 mM HEPES buffer at concentration of 20 mg/ml, and the pH was adjusted to 4 approx. with NaOH. Retained and released ZA was quantified by HPLC. This figure shows that the absolute amount of retained ZA is proportional to DOTMA, and the total lipid concentration in the colloid.

FIG. 3 shows the release of ZA from ZA colloidal dispersion after binding to RNA. Colloidal lipid dispersion comprising ZA where the total molar fraction of lipid was varied were mixed with PBS as a control, RNA, or Triton x100. The lipid composition was DOTMA/DOPE in a 2/1 molar ratio. ZA/lipid dispersions were prepared by mixing a calculated volume of lipid dispersions comprising ZA with the calculated volume of RNA at three different lipid concentrations 2, 4, and 6 mM. The ZA/lipid dispersions and RNA were mixed at 1:1 ratio (v/v). The cationic lipid/RNA charge ratio was Cationic lipid/RNA (mole/base)=1/2. For PBS and Tritonx100, the calculated RNA volume was replaced by physiological PBS or Triton x100 aqueous solution of 10%. The LNPs comprising ZA and RNA were incubated for 30 minutes at room temperature. Afterwards, the free ZA was determined by HPLC as mentioned above. The results indicate that complexation of the ZA colloidal dispersion with RNA leads to retention of the majority of ZA; only minor percentages of 0, 23, and 22% retained ZA were released with respect to total lipid concentrations of 2, 4, and 6 mg/ml, respectively. This finding was confirmed by substitution of RNA with Triton x100 (as a negative control) which led to 100% release of retained ZA. In vivo results in which IPP accumulation was detected in kidney and bone marrow support these results.

FIG. 4 shows the Cryo-Transmission Electron Microscopy (Cryo-TEM) of LNPs comprising ZA and RNA. The lipid composition of the LNPs was DOTMA/DOPE 2/1 molar ratio, they contained RNA at a positive/negative (cationic lipid/RNA nucleotide) ratio of 1.3:2. Final lipid concentration was 0.3 mM. After assembly, the formulations were incubated for 30 minutes at RT before Cryo-TEM measurements. As shown in all images the particles have a size of about 200 nm to 400 nm, with an internal lamellar organization. The number of organized lamellae varies and is estimated to range from 2 to 10 units.

FIG. 5 shows the expression of luciferase IVT-RNA in DCs after incubation with ZA-containing LNPs in comparison to naked RNA in vitro. The luciferase expression was evaluated via luminescence indicating the metabolic rate of luciferin as substrate for luciferase in counts per seconds (cps). In total, iDCs of two donors have been tested separately and the mean value is shown including SD. Incubation with ZA-containing LNPs leads to a remarkable expression in DCs.

FIG. 6 shows the relative expression of maturation markers after in vitro incubation of dendritic cells with ZA-containing LNPs (with or without RNA) compared to a positive control (maturation cocktail containing IL-4, GM-CSF, IL-1β, TNF-α, IL-6 and PGE-2). Here, the relative expression of CD83 (A), CD86 (B) and HLA-DR (C) is shown. Expression data were normalized to no stimulation control. In total, four donors have been tested separately and the mean value is shown including SD.

FIG. 7 shows the relative expression of maturation markers in dendritic cells in vitro. In order to determine the influence of LNPs (i.e. RNA bound to colloidal ZA/lipid dispersion) on the maturation of dendritic cells (DCs) in vitro compared to a positive control (maturation cocktail containing IL-4, GM-CSF, IL-1ß, TNF-α, IL-6 and PGE-2), naked RNA and colloidal ZA/lipid dispersion (i.e. zoledronic acid (ZA) entrapped in colloidal dispersion). Dendritic cells were incubated over 24 h and 48 h with ZA-containing LNPs in 3 different ZA-concentrations (0.5, 5 and 50 µM). Here, the relative expression of maturation markers CD80 (A), CD83 (B), CD86 (C) and HLA-DR (D) is shown. In total, 2 donors have been tested separately and the mean value is shown including SD.

FIG. 8 shows the IPP accumulation in DCs in vitro as a measure for cellular ZA uptake. Dendritic cells were incubated over-night with different formulations of ZA, meaning free ZA or formulated in LNPs in a dose-range from 0.1-125 µM. In this assay, only if ZA is available intracellularly, an increase of IPP concentration is expected. LNPs comprising ZA and RNA were tested in comparison to free ZA. Free ZA as well as formulated in LNPs show dose-dependency regarding accumulation of IPP, however with the ZA in the LNPs, much lower doses (at least one order of magnitude) were necessary to induce elevated IPP values. This indicates, that the LNPs were functional as a carrier to provide uptake of the ZA to the cytosol of the cells.

FIG. 9 shows the in vivo activity and effects of LNPs comprising ZA and RNA encoding for Luciferin. 6 h after i.v. injection of LNPs comprising ZA and RNA encoding for Luciferin, the LNPs are (A) able to specifically target spleen tissue, leading to in vivo detectable bioluminescence signal. Furthermore, analysed 24 h after injection, splenic cell populations show, that (B) LNPs comprising ZA complexed with eGFP-RNA mainly targets antigen-presenting cells such as dentritic cells (DCs), macrophages (mΦ) and monocytes and (C) is able to upregulate the expression of maturation marker CD86 on splenic DCs and macrophages compared to untreated mice (cntr).

FIG. 10 shows tissue IPP levels after administration of RNA and ZA comprising LNPs to mice. 6, 24 and 48 h after i.v. injection of LNPs comprising ZA complexed with RNA encoding for Luciferin and at a dose of 1.5 µg Zoledronic acid (ZA)/mouse injected, increased IPP levels in lung, liver and spleen of treated mice compared to tissue of untreated mice are observed. Highest IPP levels are observed after 24 h and for spleen tissue (1 animal/time-point). This indicates that the LNPs comprising ZA and RNA can deliver the ZA to the cytosolic compartment of the target cells.

FIG. 11 shows isopentenylpyrophosphate (IPP) accumulation after incubation of three different concentrations of Zoledronic acid and (Luc) RNA encapsulating LNPs with DCs. In contrast, untreated group or application of free ZA did not increase IPP values.

Zoledronic acid resulted in accumulation of isopentenylpyrophosphate (IPP) in the spleen>lung>liver. Application of Zoledronic acid and (Luc) RNA encapsulating LNPs resulted in an accumulation of isopentenylpyrophosphate (IPP) in spleen>lung>liver. In contrast, untreated group did not increase IPP values. Bars represent mean IPP values of 3 animals 24 h after i.v. administration.

FIG. 13

Panel A is an in vivo imaging picture showing the biodistribution of LNPs (LNP2-4) in vivo. Panel B shows a graph ("quantification") of the Luciferase signal measured in the region of interest which here is spleen location. Panel C shows the activation (Maturation) status of splenic DC cells extracted 24 h after injection of LNP2-4.

FIG. 14

Figure 5:
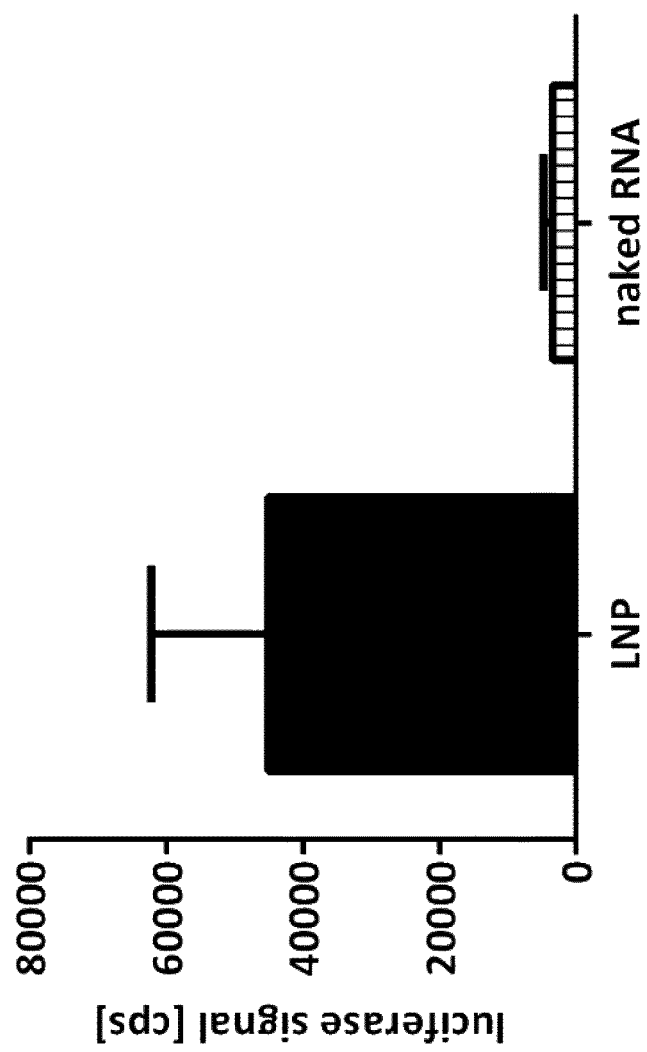
FIG. 5

According to FIG. 5, here the expression of luciferase IVT-RNA in DCs after incubation with different ZA-containing LNPs in vitro is shown. The luciferase expression was evaluated via luminescence indicating the metabolic rate of luciferin as substrate for luciferase in counts per seconds (cps). In total, iDCs of two donors have been tested separately and the mean value is shown including SD. Depart from LNP-4, the other ZA-containing LNPs Incubation with the other ZA-containing LNPs, LNP-2 and LNP-3, lead to a remarkable expression in DCs.

FIG. 15

Figure 7:
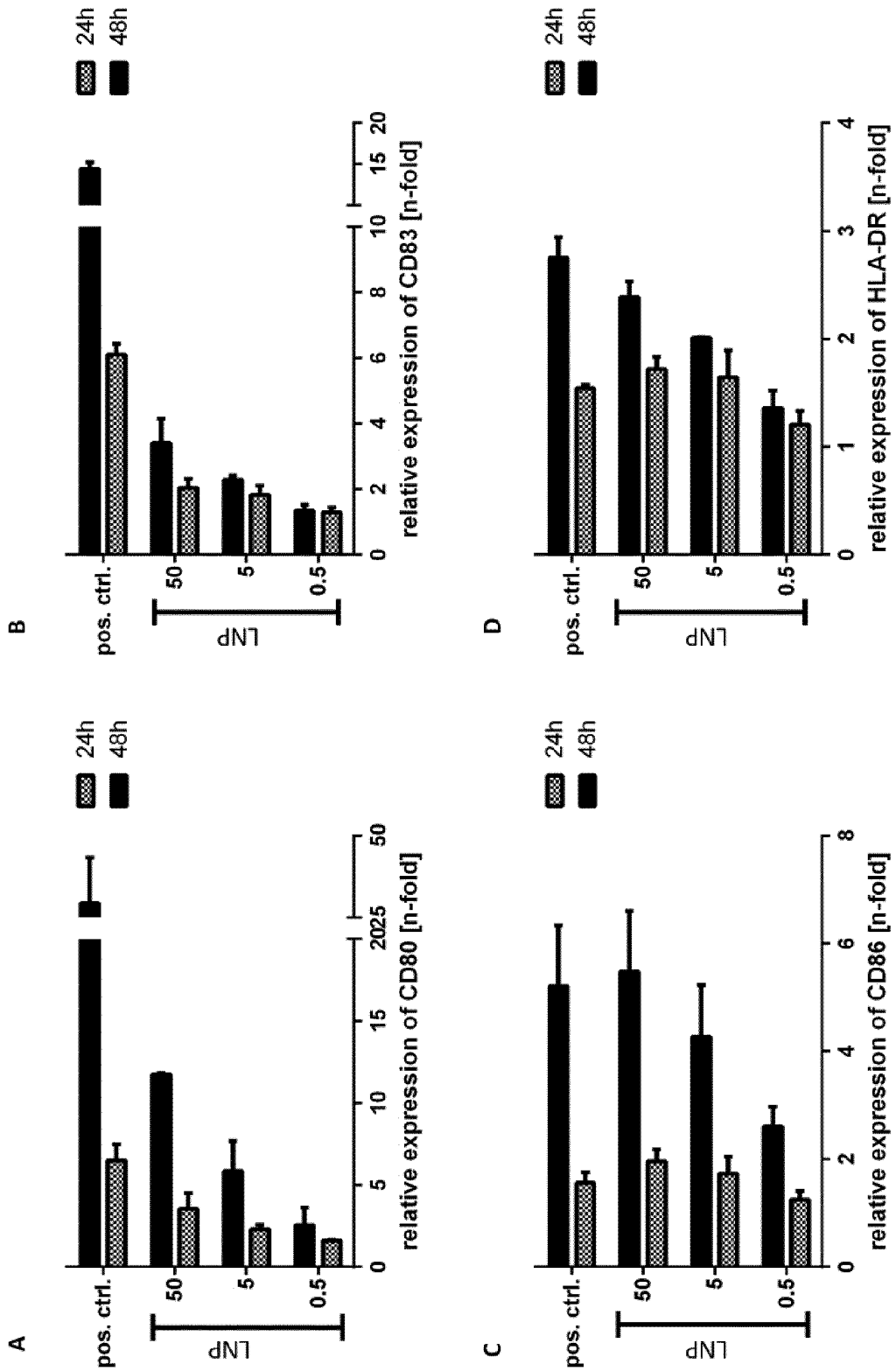
FIG. 7.
Figure 8:
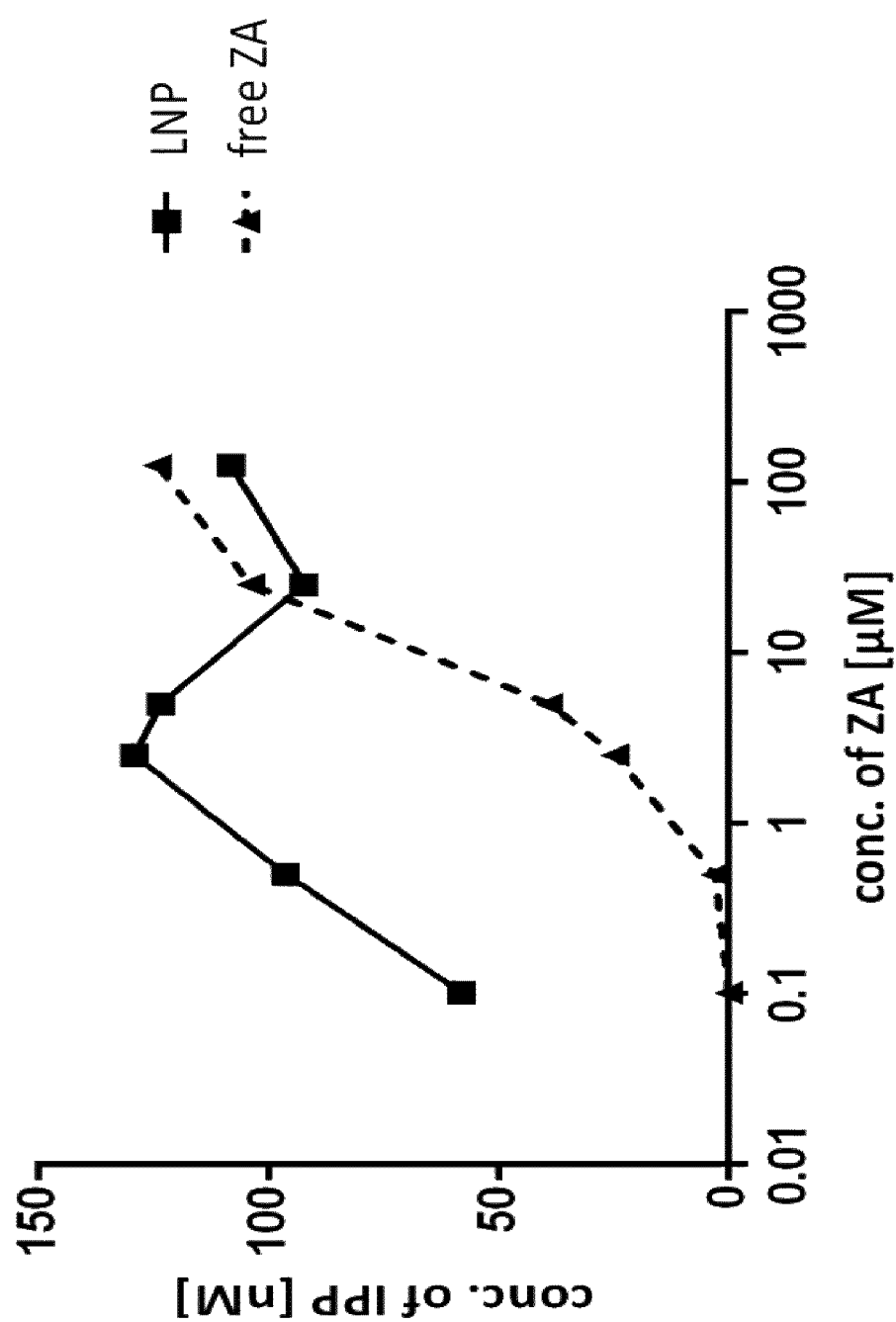
FIG. 8
Figure 9:
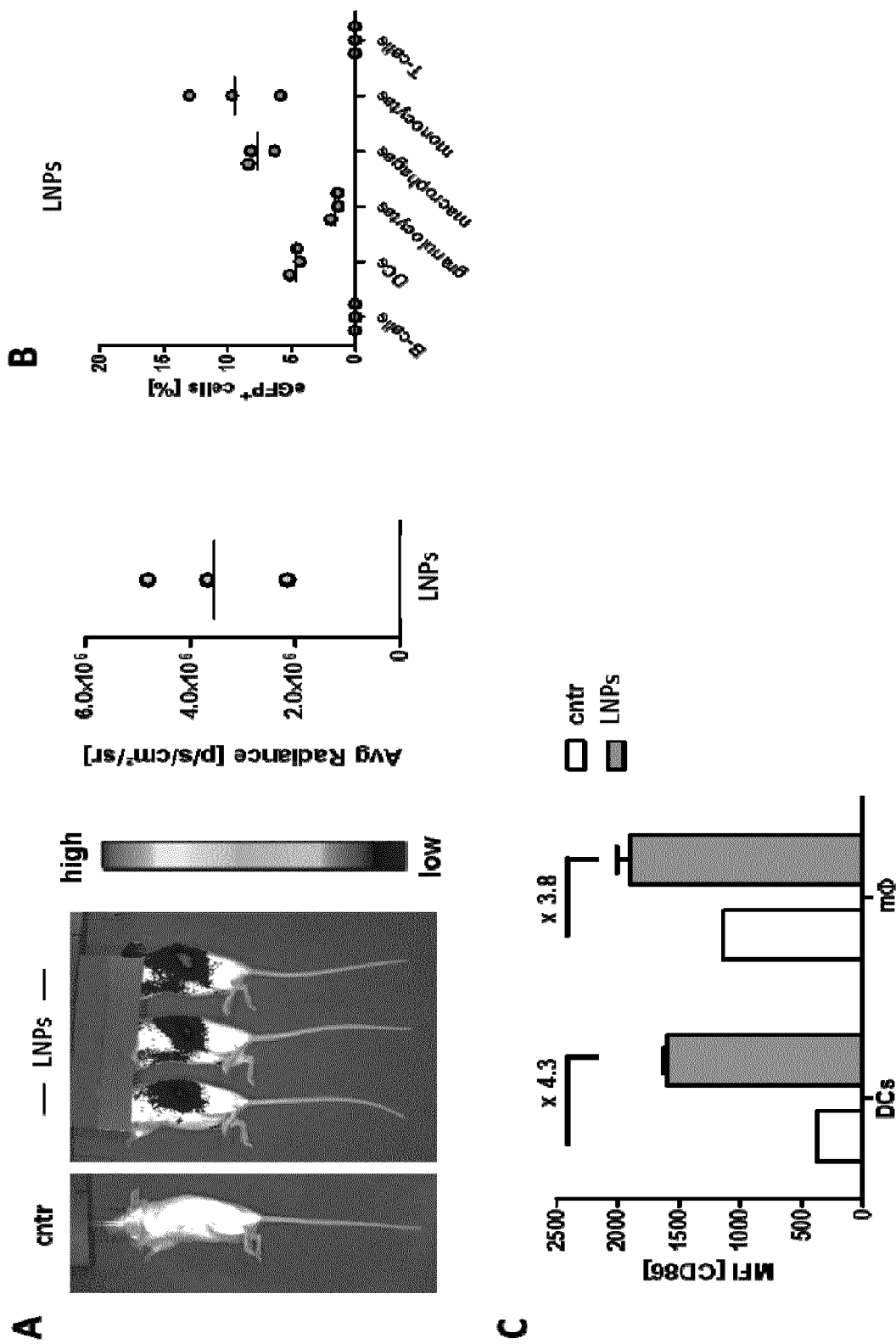
FIG. 9
Figure 10:
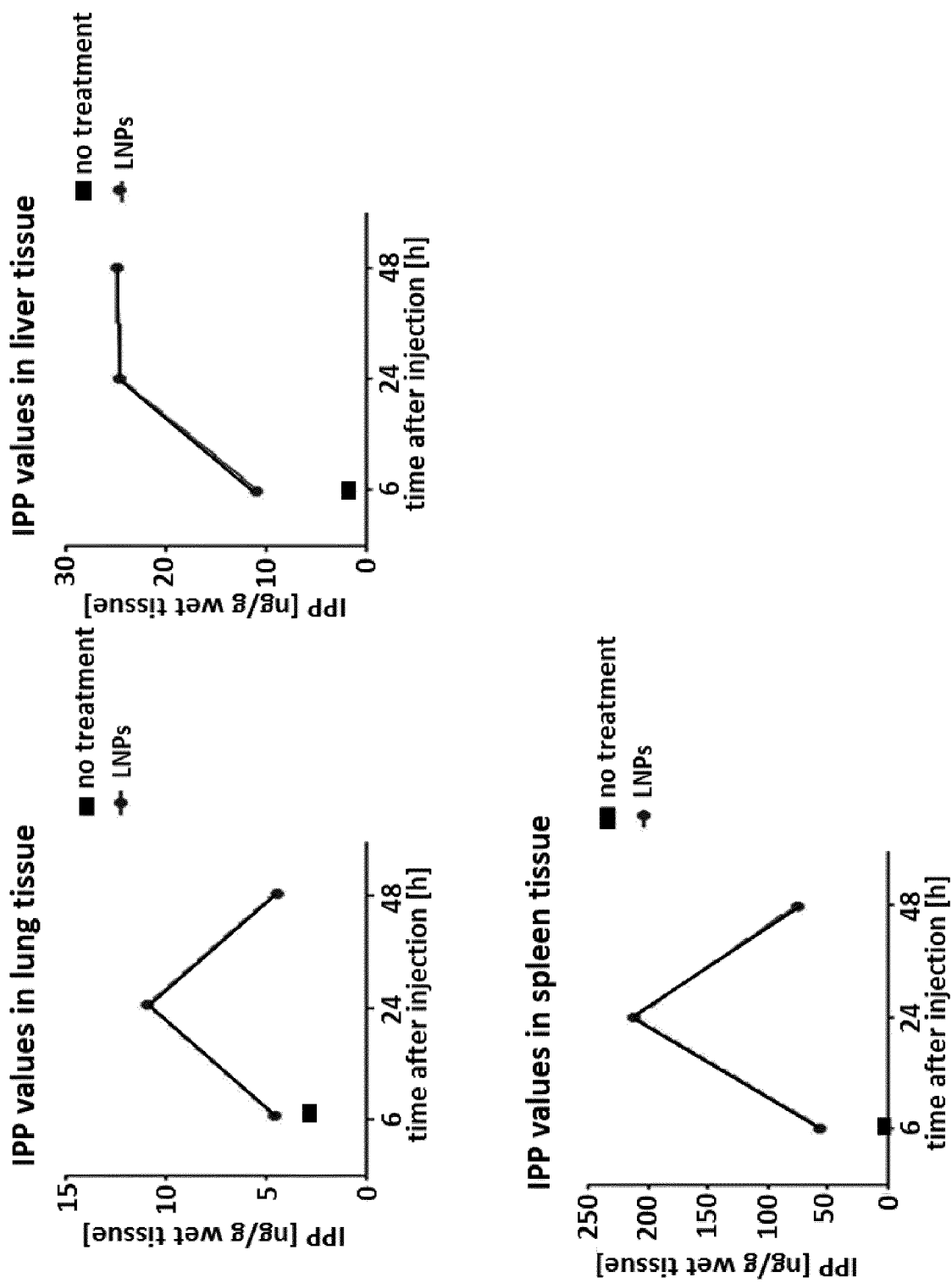
FIG. 10
Figure 11:
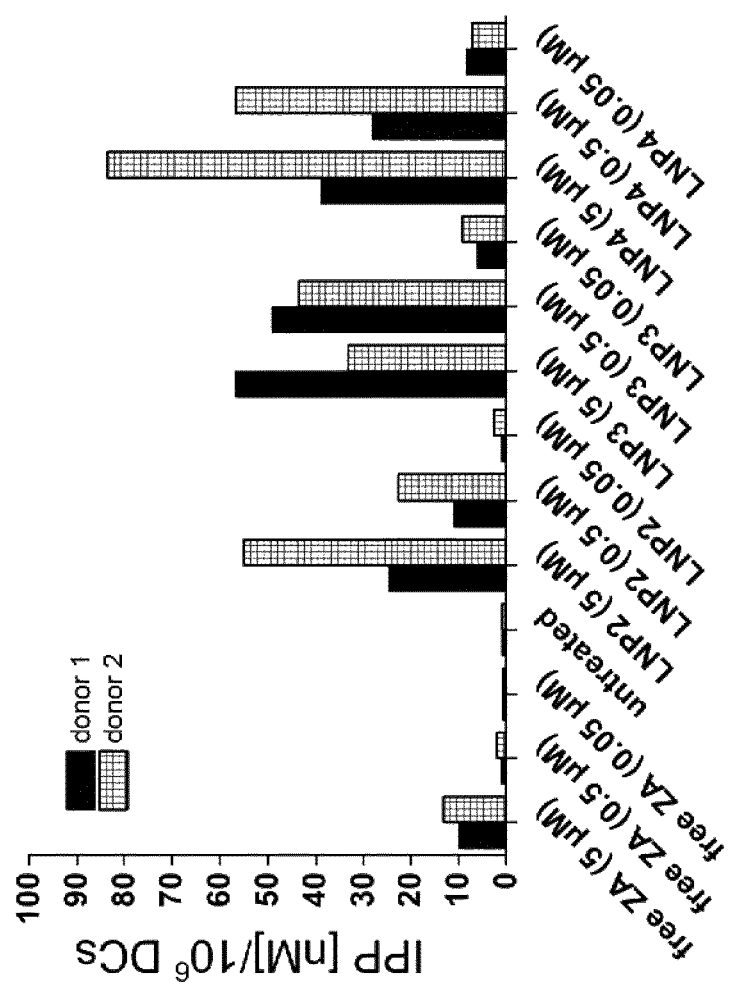
FIG. 11
Figure 12:
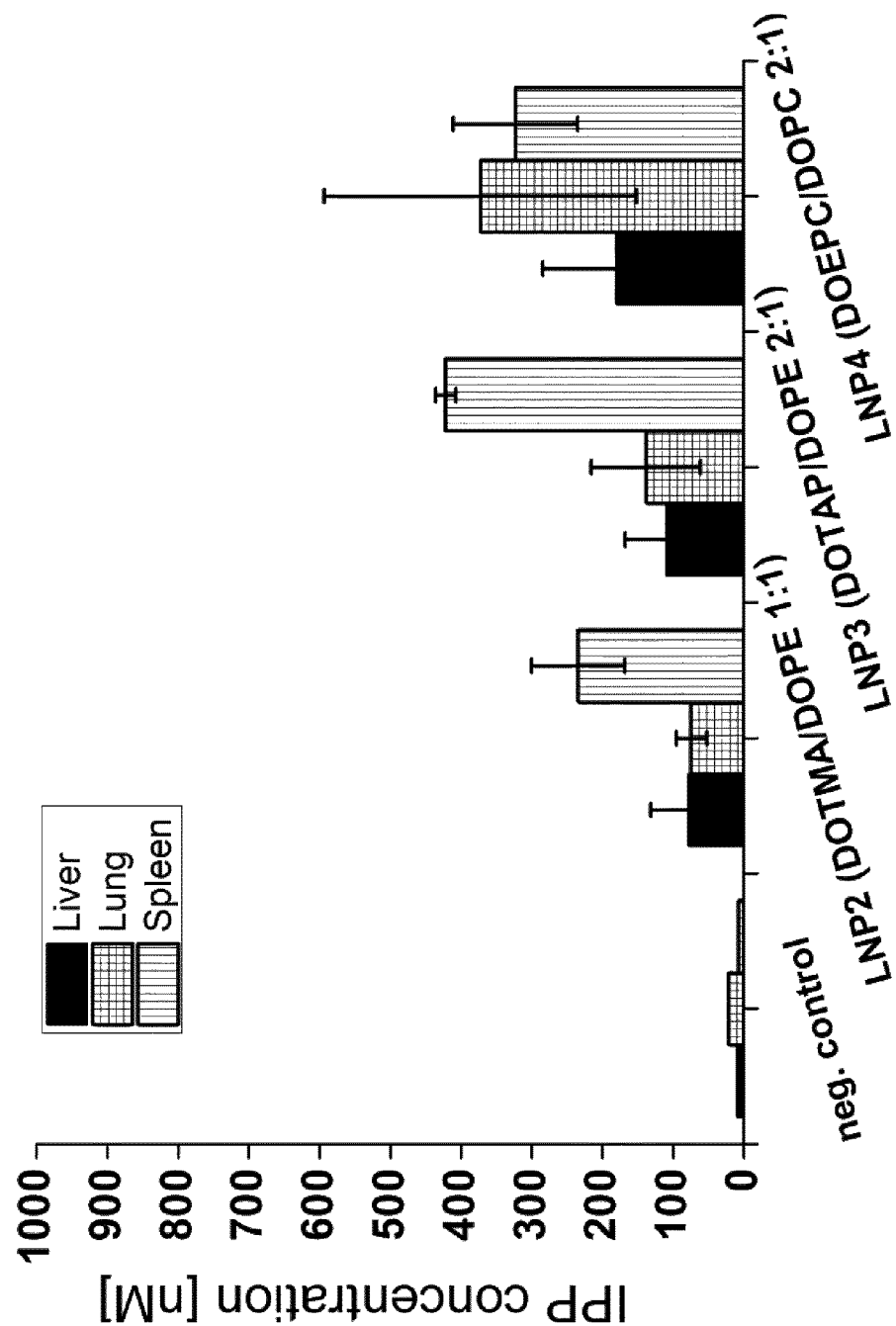
FIG. 12
Figure 13:
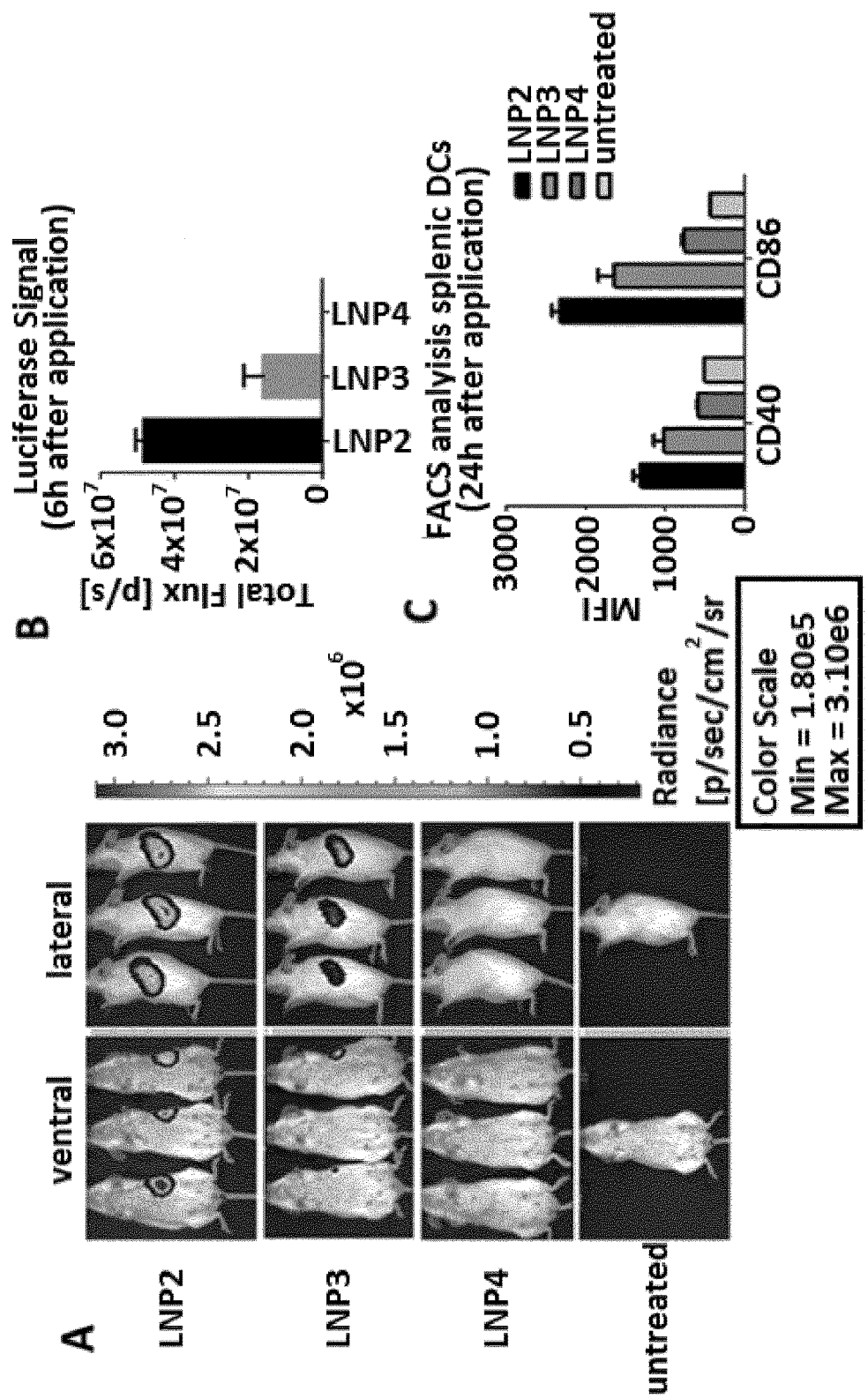
Figure 14:
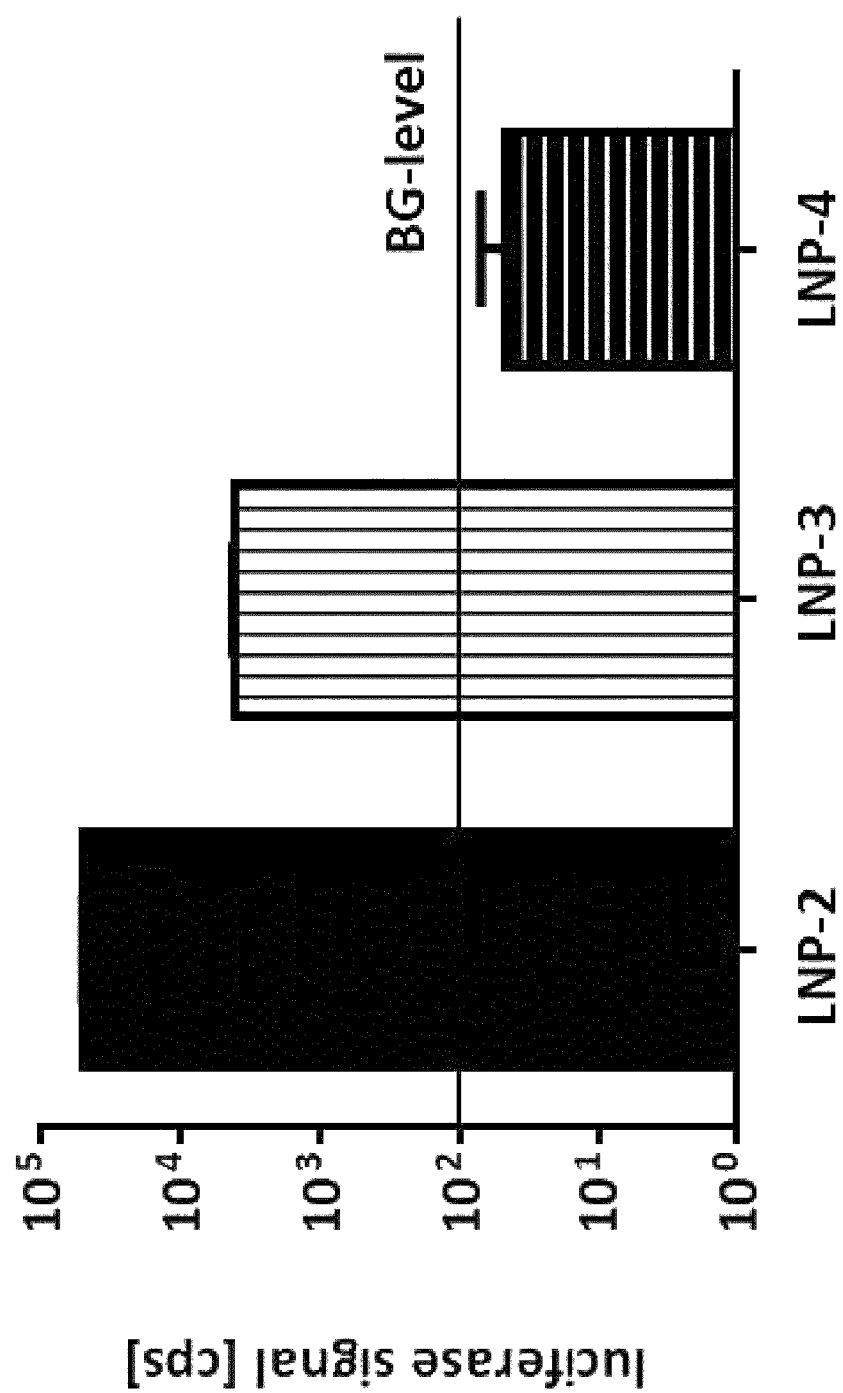
Figure 15:
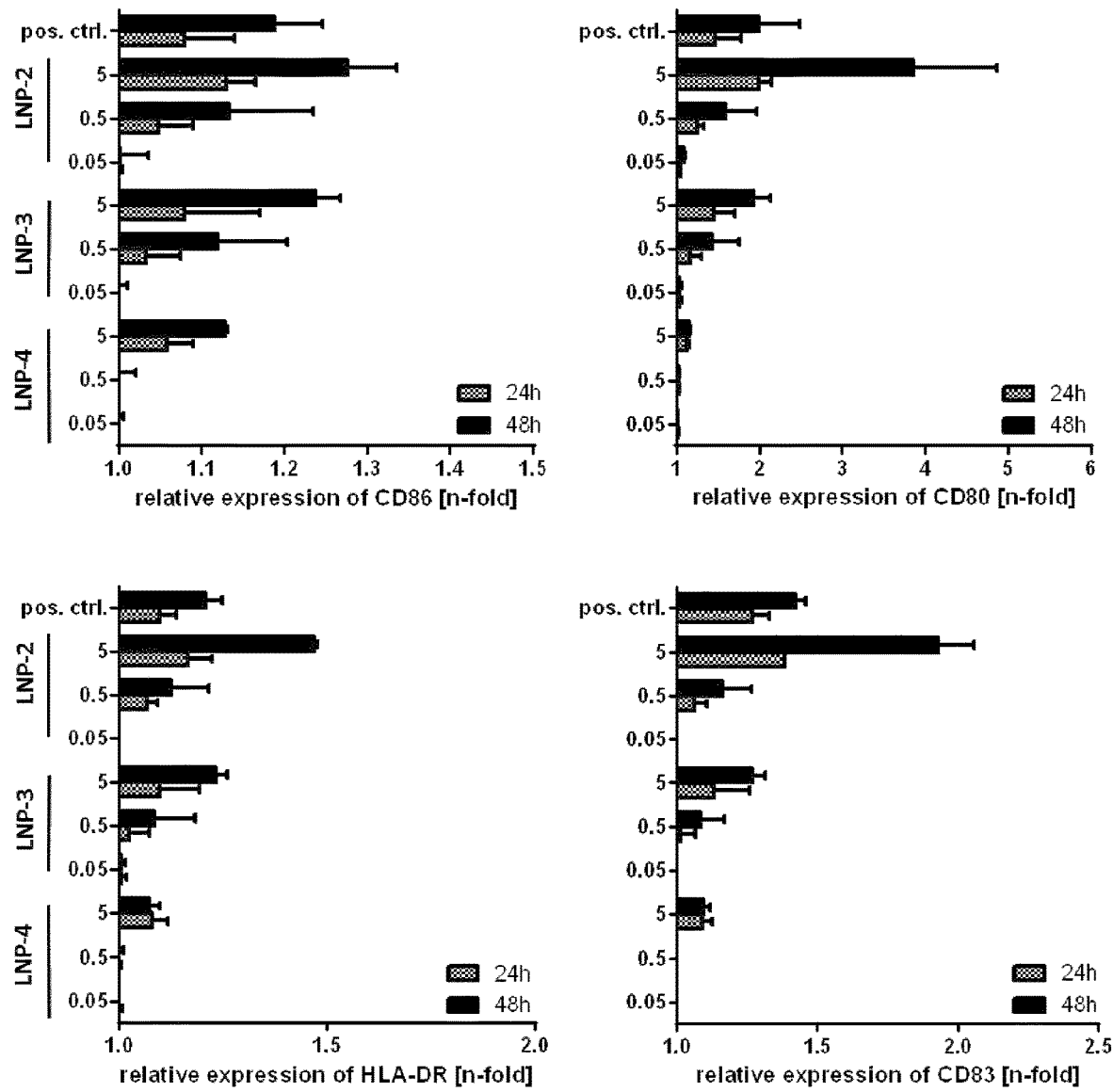

According to FIG. 7, here, the relative expression of maturation markers in dendritic cells in vitro is shown. In order to determine the influence of different LNPs (i.e. RNA bound to colloidal ZA/lipid dispersion) on the maturation of dendritic cells (DCs) in vitro compared to a positive control (maturation cocktail containing IL-4, GM-CSF, IL-1ß, TNF-α, IL-6 and PGE-2) dendritic cells were incubated over 24 h and 48 h with different ZA-containing LNPs in 3 different ZA-concentrations (0.05, 0.5 and 5 µM). Here, the relative expression of maturation markers CD80 (A), CD83 (B), CD86 (C) and HLA-DR (D) is shown. In total, 2 donors have been tested separately and the mean value is shown including SD.

FIG. 16

Figure 16:
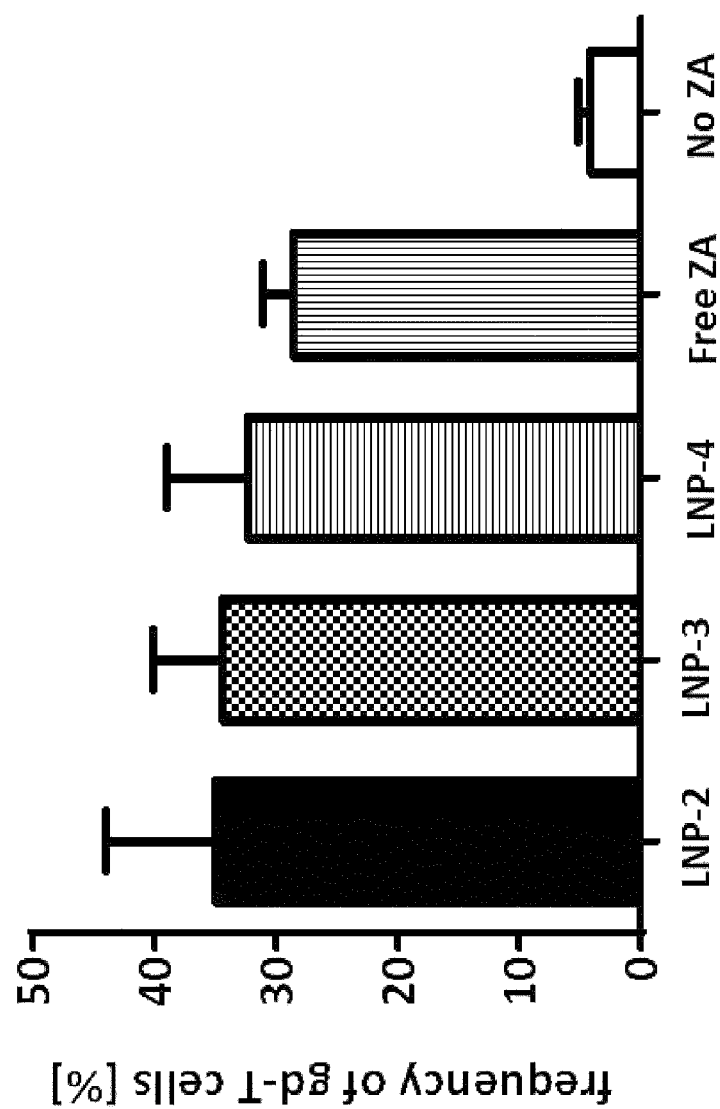

FIG. 16 shows the frequency of γ9δ2 T cells after cocultivation of ZA-loaded iDCs with cryopreserved PBLs. In order to determine whether the retained compound, ZA, is still functional, iDCs have been loaded for 24 h with different ZA-containing LNPs and subsequentially coincubated with PBLs for 7 days. The expansion of γ9δ2 T cells, meaning an increased frequency, have been finally evaluated via flow cytometry. In two different donors, tested independently, it could be observed that the retaining compound, ZA, in all different LNPs is still functional and leads to even higher frequency of γ9δ2 T cells compared to free ZA.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a preferred embodiment the particle of the present invention comprises a water-soluble therapeutically effective compound and if in another preferred embodiment the particle of the present invention comprises RNA encoding at least one antigen, it is a contemplated preferred embodiment that the particle of the present invention comprises a water-soluble therapeutically effective compound and RNA encoding at least one antigen.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In the following, definitions will be provided which apply to all aspects of the present invention.

In the context of the present invention, the term "particle" relates to a structured entity formed by molecules or molecule complexes. In one embodiment, the term "particle" relates to a micro- or nano-sized structure, such as a micro- or nano-sized compact structure.

In the context of the present invention, the term "lipid particle" relates to a particle that contains lipid, in particular cationic lipid.

In one embodiment, the particles of the present invention have an average diameter in the range of from about 50 nm to about 1000 nm, e.g. from about 100 nm to about 900 nm, from about 200 nm to about 800 nm, from about 200 to about 700 nm, from about 300 to about 600 nm, from about 300 nm to about 500 nm, or from about 300 nm to about 400 nm.

In one embodiment, the particles of the present invention have an average diameter of at least about 50 nm, at least about 60 nm, at least about 70 nm, at least about 80 nm, at least about 90 nm, at least about 100 nm, at least about 150 nm, at least about 200 nm, at least about 250 nm, at least about 300 nm, at least about 400 nm, at least about 500 nm, at least about 600 nm, at least about 700 nm, at least about 800 nm, at least about 900 nm, and/or the particles of the present invention have an average diameter of no more than about 1000 nm, no more than about 900 nm, no more than about 800 nm, no more than about 700 nm, no more than about 600 nm, no more than about 500 nm, no more than about 400 nm, no more than about 300 nm, no more than about 250 nm, no more than about 200 nm, no more than about 150 nm, no more than about 100 nm, no more than about 90 nm, no more than about 80 rum, no more than about 70 nm, no more than about 60 nm.

In one preferred embodiment, the particles of the present invention have an average diameter (i) in the range of from about 50 nm to about 400 nm, preferably from about 50 nm to about 200 nm, or (ii) in the range of from about 200 nm to about 1000 nm, preferably from about 200 nm to about 800 nm, more preferably from about 300 nm to about 600 nm.

The particles of the invention may comprise a lipid structure capable of receiving and/or retaining a therapeutically effective compound and capable of receiving and/or retaining the RNA, preferably by binding of the RNA to cationic lipid comprised in the lipid structure. In other words, the inside of the lipid structure may be structured such that a therapeutically effective compound is loaded to it. Such lipid structures may have high lipid content. According to the present invention, the term "lipid" refers to any fatty acid derivative or other amphiphilic compound which is capable of forming a lyotropic lipid phase, or more preferentially, a lamellar lyotropic phase. In particular, the term "lipid" refers to any fatty acid derivative which is capable of forming a bilayer such that a hydrophobic part of the lipid molecule orients toward the bilayer while a hydrophilic part orients toward the aqueous phase. The term "lipid" comprises neutral, anionic or cationic lipids. Lipids preferably comprise a hydrophobic domain with at least one, preferably two, alkyl chains or a cholesterol moiety and a polar head group. The alkyl chains of the fatty acids in the hydrophobic domain of the lipid are not limited to a specific length or number of double bonds. Nevertheless, it is preferred that the fatty acid has a length of 10 to 30, preferably 14 to 25 carbon atoms. The lipid may also comprise two different fatty acids.

The lipids may include phospholipids or derivatives thereof, sphingolipids or derivatives thereof, or glycolipids or derivatives thereof. The phospholipids may be glycerophospholipids. Examples of a glycerophospholipid include, without being limited thereto, phosphatidylglycerol (PG) including dimyristoyl phosphatidylglycerol (DMPG); phosphatidylcholine (PC), including egg yolk phosphatidylcholine and dimyristoyl phosphatidylcholine (DMPC); phosphatidic acid (PA), phosphatidylinositol (PI), phosphatidylserine (PS) and sphingomyelin (SM) and derivatives of the same.

The term "cationic lipid" refers to a lipid having a net positive charge. The cationic lipid preferably comprises a cationic, meaning positively charged, headgroup. The hydrophobic domain of cationic lipids is preferably not different from neutral or anionic lipids. The polar headgroup of the cationic lipids preferably comprises amine derivatives such as primary, secondary, and/or tertiary amines, quaternary ammonium, various combinations of amines, amidinium salts, or guanidine and/or imidazole groups as well as pyridinium, piperizine and amino acid headgroups such as lysine, arginine, ornithine and/or tryptophan. More preferably, the polar headgroup of the cationic lipid comprises amine derivatives. Most preferably, the polar headgroup of the cationic lipid comprises a quaternary ammonium. The headgroup of the cationic lipid may comprise multiple cationic charges. It is preferred, that the headgroup of the cationic lipid comprises one cationic charge. Monocationic lipids include 1,2-dimyristoyl-sn-glycero-3-ethylphosphocholine (DMEPC), 1,2-di-O-octadecenyl-3-trimethylammonium propane (DOTMA) and/or 1,2-dioleoyl-3-trimethylammonium propane (DOTAP), 1,2-dimyristoyl-3-trimethylammonium propane (DMTAP), 2,3-di(tetradecoxy)propyl-(2-hydroxyethyl)-dimethylazanium bromide (DMRIE), didodecyl(dimethyl)azanium bromide (DDAB), 1,2-dioleyloxypropyl-3-dimethyl-hydroxyethyl ammonium bromide (DORIE), 3β-[N—(N\N'-dimethylamino-ethane)carbamoyl]cholesterol (DC-Chol) or dioleyl ether phosphatidylcholine (DOEPC), but are not limited thereto. The cationic lipids may be used alone or in combination with cholesterol, with neutral phospholipids or other known lipid assembly components. The positively charged lipid structures described herein may also include other components typically used in the formation of vesicles (e.g. for stabilization). Examples of such other components includes, without being limited thereto, fatty alcohols, fatty acids, and/or cholesterol esters or any other pharmaceutically acceptable excipients which may affect the surface charge, the membrane fluidity and assist in the incorporation of the lipid into the lipid assembly. Examples of sterols include cholesterol, cholesteryl hemisuccinate, cholesteryl sulfate, or any other derivatives of cholesterol. Preferably, the at least one cationic lipid comprises DMEPC and/or DOTMA.

According to the present invention, the term "cationic lipid" also includes pH responsive lipids. The term "pH responsive lipid" refers to any fatty acid derivative or other amphiphilic compound which is capable of forming a lyotropic lipid phase, and which has a pKa value between pH 5 and pH 7.5. This means that the lipid is uncharged at a pH above the pKa value and positively charged below the pKa value. The "pH responsive lipid" may be used in addition to or instead of a cationic lipid for example by binding the RNA to the lipid or lipid mixture at low pH. pH responsive lipids include, but are not limited to, 1,2-dioleyloxy-3-dimethylamino-propane (DODMA)

The term "helper lipid" refers to a lipid capable of increasing the effectiveness of delivery of lipid-based particles such as cationic lipid-based particles to a target, preferably into a cell. The helper lipid can be neutral, positively charged, or negatively charged. Preferably, the helper lipid is neutral or negatively charged. Examples for helper lipids include 1,2-di-(9Z-octadecenoyl)-sn-glycero-3-phosphoethanolamine (DOPE), cholesterol (Chol), 1-palmitoyl-2-oleoyl-sn-glycero-3phosphocholin (POPC) and 1,2-dioleoyl-sn-glycero-3-phosphocholine (DOPC), but are not limited thereto. Preferably, the at least one helper lipid comprises DOPE, and/or Chol.

In one embodiment, the at least one cationic lipid comprises DOTMA and the at least one helper lipid comprises DOPE or DOPC or derivatives thereof, or Cholesterol or derivatives thereof.

As used herein, the term "lamellar structure" or "lamellar organization" means the formation of layers in lamellar form.

The term "ethanol injection technique" refers to a process, in which an ethanol solution comprising lipids is rapidly injected into an aqueous solution through a needle. This action disperses the lipids throughout the solution and promotes lipid structure formation, for example lipid vesicle formation such as liposome formation.

Using the ethanol injection technique, a colloidal lipid dispersion comprising a therapeutically effective compound is preferably formed as follows: an ethanol solution comprising lipids, such as cationic lipids like DMEPC, DOTMA and DOTAP and helper lipids, is injected into an aqueous solution comprising a therapeutically effective compound, e.g. a bisphosphonate, particularly aminobisphosphonate like zoledronic acid, e.g. under stirring.

The particles of the present invention are obtainable by adding RNA to a colloidal lipid dispersion comprising the therapeutically effective compound. In one embodiment, the particles of the present invention are obtainable by a process comprising a step of extruding and/or a step of lyophilizing the particle. Preferably, the particles are extruded, e.g. by filtration, through a membrane having pores with a diameter of 0.02 to 1 µm, preferably of 0.3 to 0.6 µm or between 0.02 and 0.2 µm. It is to be understood, that the size of the pores are chosen in dependence of the desired size of the particles. It is preferred, that the membrane is a polycarbonate membrane or cellulose ester membrane. The not retained therapeutically effective compound is preferably removed via dialysis.

In another embodiment, the particles of the present invention are obtainable without a step of extrusion.

The term "extruding" or "extrusion" refers to the creation of objects such as particles having a fixed, cross-sectional profile. In particular, it refers to the downsizing of a particle, preferably a liposome, whereby the particle is forced through filters with defined pores.

The term "lyophilizing" or "lyophilization" refers to the freeze-drying of a particle by freezing it and then reducing the surrounding pressure to allow the frozen medium in the particle to sublimate directly from the solid phase to the gas phase.

The term "therapeutically effective compound" relates to any compound being therapeutically effective when administered to an individual. The term "therapeutically effective compound" further relates to any agent that changes, preferably cures, alleviates or partially arrests the clinical manifestations of a given disease and its complications in a therapeutic intervention comprising the administration of said compound.

In one embodiment, the therapeutically effective compound in the particles of the present invention is water-soluble. Hydrophilic properties of the therapeutically effective compound may improve its loading efficiency and prevent undesired release. It is preferred, that the therapeutically effective compound has a net negative charge. It is more preferred that the therapeutically effective compound is double negatively charged. In one embodiment, the therapeutically effective compound is a small molecule. A small size of the compound may further improve the encapsulating efficiency. Small molecule compounds are described to act as good antagonist, agonists or allosteric modulators of diverse targets.

In the present context, the term "treatment", "treating" or "therapeutic intervention" relates to the management and care of an individual for the purpose of combating a condition such as a disease or disorder. The term is intended to include the full spectrum of treatments for a given condition from which the individual is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications. The individual to be treated is an animal, preferably a mammal, in particular a human being. In the present context, the term "therapeutically effective amount" of a compound means an amount sufficient to cure, alleviate or partially arrest the clinical manifestations of a given disease and its complications in a therapeutic intervention comprising the administration of a compound. The desired reaction for a therapy of a disease or a condition may also be the retardation of the occurrence or the inhibition of the occurrence of the disease or the condition. An therapeutically effective amount of a compound according to the present invention is dependent on the condition or disease, the severity of the disease, the individual parameters of the individual, including age, physiological condition, height, and weight, the duration of the treatment, the type of an optionally accompanying therapy, the specific administration route, and similar factors.

In the context of the present invention, the term "RNA" relates to a molecule which comprises ribonucleotide residues and preferably being entirely or substantially composed of ribonucleotide residues and comprises all RNA types described herein. The term "ribonucleotide" relates to a nucleotide with a hydroxyl group at the 2'-position of a β-D-ribofuranosyl group. The term "RNA" comprises double-stranded RNA, single stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs, particularly analogs of naturally-occurring RNAs. The RNA used according to the present invention may have a known composition, or the composition of the RNA may be partially or entirely unknown. The term "mRNA" means "messenger-RNA" and relates to a transcript which is generated by using a DNA template and encodes a peptide or protein. Typically, mRNA comprises a 5'-UTR, a protein coding region, and a 3'-UTR. mRNA may be generated by in vitro transcription from a DNA template. The in vitro transcription methodology is known to the skilled person. For example, there is a variety of in vitro transcription kits commercially available. The term "anti-sense-RNA" relates to single-stranded RNA comprising ribonucleotide residues, which are complementary to the mRNA. The term "siRNA" means "small interfering RNA", which is a class of double-stranded RNA-molecules preferably comprising 20 to 25 base pairs. Preferably, siRNA is capable of binding specifically to a portion of the mRNA-molecule. This binding induces a process, in which the said portion of the mRNA-molecule is cut and thereby the gene expression of said mRNA-molecule inhibited. The term "microRNA" refers to a non-coding single-stranded RNA molecule preferably comprising 20 to 25 base pairs. Preferably, microRNA is capable of binding specifically to a portion of the mRNA-molecule. This binding induces a process, in which the translation of the said mRNA molecule and thereby the gene expression of said mRNA molecule is inhibited. The RNA may be modified by a 5'-cap or 5'-cap analog, e.g. achieved by in vitro transcription of a DNA template in presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus. The RNA may comprise further modifications. For example, a further modification of the RNA used in the present invention may be an extension or truncation of the naturally occurring poly (A) tail or an alteration of the 5'- or 3'-untranslated regions (LTTR) such as introduction of a UTR which is not related to the coding region of said RNA.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention preferably is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

The cDNA containing vector template may comprise vectors carrying different cDNA inserts which following transcription results in a population of different RNA molecules optionally capable of expressing different peptides or proteins or may comprise vectors carrying only one species of cDNA insert which following transcription only results in a population of one RNA species capable of expressing only one peptide or protein. Thus, it is possible to produce RNA capable of expressing a single peptide or protein only or to produce compositions of different RNAs capable of expressing more than one peptide or protein, e.g. a composition of peptides or proteins.

The term "expression" is used herein in its broadest meaning and comprises the production of RNA or of RNA and protein. With respect to RNA, the term "expression" or "translation" relates in particular to the production of peptides or proteins. Expression may be transient or may be stable.

According to the present invention, the RNA can be coding RNA, i.e. RNA encoding a peptide or protein. Said RNA may express the encoded peptide or protein. For example, said RNA may be RNA encoding and expressing an antigen or an immunologically active compound (which does not encode an antigen). Alternatively, the RNA can be non-coding RNA such as antisense-RNA, micro RNA (miRNA) or siRNA.

A "pharmaceutically active RNA" is a RNA that encodes a pharmaceutically active peptide or protein or is pharmaceutically active in its own, e.g., it has one or more pharmaceutical activities such as those described for pharmaceutically active proteins. For example, the RNA may be one or more strands of RNA interference (RNAi). Such agents include short interfering RNAs (siRNAs), or short hairpin RNAs (shRNAs), or precursor of a siRNA or microRNA-like RNA, targeted to a target transcript, e.g., a transcript of an endogenous disease-related transcript of a subject.

A "pharmaceutically active peptide or protein" has a positive or advantageous effect on the condition or disease state of a subject when administered to the subject in a therapeutically effective amount. Preferably, a pharmaceutically active peptide or protein has curative or palliative properties and may be administered to ameliorate, relieve, alleviate, reverse, delay onset of or lessen the severity of one or more symptoms of a disease or disorder. A pharmaceutically active peptide or protein may have prophylactic properties and may be used to delay the onset of a disease or to lessen the severity of such disease or pathological condition. The term "pharmaceutically active peptide or protein" includes entire proteins or polypeptides, and can also refer to pharmaceutically active fragments thereof. It can also include pharmaceutically active analogs of a peptide or protein. The term "pharmaceutically active peptide or protein" includes peptides and proteins that are antigens, i.e., administration of the peptide or protein to a subject elicits an immune response in a subject which may be therapeutic or partially or fully protective.

Examples of pharmaceutically active proteins include, but are not limited to, cytokines and immune system proteins such as immunologically active compounds (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, seletins, homing receptors, T cell receptors, immunoglobulins, soluble major histocompatibility complex antigens, immunologically active antigens such as bacterial, parasitic, or viral antigens, allergens, autoantigens, antibodies), hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, enzymes (tissue plasminogen activator, streptokinase, cholesterol biosynthestic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases and the like), receptors (steroid hormone receptors, peptide receptors), binding proteins (growth hormone or growth factor binding proteins and the like), transcription and translation factors, tumor growth suppressing proteins (e.g., proteins which inhibit angiogenesis), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, protein C, von Wilebrand factor, antithrombin III, glucocerebrosidase, erythropoietin granulocyte colony stimulating factor (GCSF) or modified Factor VIII, anticoagulants and the like.

In one embodiment, the pharmaceutically active protein according to the invention is a cytokine which is involved in regulating lymphoid homeostasis, preferably a cytokine which is involved in and preferably induces or enhances development, priming, expansion, differentiation and/or survival of T cells. In one embodiment, the cytokine is an interleukin. In one embodiment, the pharmaceutically active protein according to the invention is an interleukin selected from the group consisting of IL-2, IL-7, IL-12, IL-15, and IL-21.

In one particularly preferred embodiment of the invention, the RNA in the particles encodes a cytokine which is involved in and preferably induces or enhances development, priming, expansion, differentiation and/or survival of T cells, preferably an interleukin such as an interleukin selected from the group consisting of IL-2, IL-7, IL-12, IL-15, and IL-21, and the at least one therapeutically effective compound retained in the particles comprises an agent stimulating $\gamma\delta$ T cells such as zoledronic acid.

According to the present invention, the term "peptide" comprises oligo- and polypeptides and refers to substances comprising two or more, preferably three or more, preferably four or more, preferably six or more, preferably eight or more, preferably ten or more, preferably 14 or more, preferably 16 or more, preferably 21 or more and up to preferably 8, 10, 20, 30, 40, or 50, in particular 100 amino acids joint covalently by peptide bonds. The term "protein" refers to large peptides, preferably to peptides with more than 100 amino acid residues, but in general the terms "peptides" and "proteins" are synonymous and are used interchangeably herein.

According to the invention, the term "RNA encoding" means that the RNA, if present in the appropriate environment, preferably within a cell, can direct the assembly of amino acids to produce the protein or peptide is encodes during the process of translation. Preferably, RNA according to the invention is able to interact with the cellular translation machinery allowing translation of the protein or peptide.

The term "net charge of the particle" relates to the total sum of charges, such as positive and negative charges. For example, if the particle comprises a higher number of negative charges than positive charges, the net charge of the particle is negative. If the particle comprises a higher number of positive charges than negative charges, the net charge of the particle is positive. If the particle comprises an equal number of positive charges and negative charges, the net charge of the particle is neutral, particularly electroneutral. Thus, the net charge of the particle according to the present invention can be negative, positive or neutral. Preferably, the net charge of the particle is negative.

The term "average diameter" refers to the mean diameter of the particles and may be calculated by dividing the sum of the diameter of each particle by the total number of particles. Although the term "diameter" is used normally to refer to the maximal length of a line segment passing through the center and connecting two points on the periphery of a spherical object, it is also used herein to refer to the maximal length of a line segment passing through the center and connecting two points on the periphery of particles having a substantial spherical shape or other shapes.

The term "antigen" relates to an agent comprising an epitope against which an immune response is to be generated. The term "antigen" includes in particular proteins, peptides, polysaccharides, nucleic acids, especially RNA and DNA, and nucleotides. The term "antigen" also includes agents, which become antigenic—and sensitizing—only through transformation (e.g. intermediately in the molecule or by completion with body protein). An antigen is preferably presentable by cells of the immune system such as antigen presenting cells like dendritic cells or macrophages. In addition, an antigen or a processing product thereof is preferably recognizable by a T or B cell receptor, or by an immunoglobulin molecule such as an antibody. In a preferred embodiment, the antigen is a disease-associated antigen, such as a tumor antigen, a viral antigen, or a bacterial antigen.

The term "tumor antigen" refers to a constituent of cancer cells which may be derived from the cytoplasm, the cell surface and the cell nucleus. In particular, it refers to those antigens which are produced, preferably in large quantity, intracellularly or as surface antigens on tumor cells. Examples for tumor antigens include HER2, EGFR, VEGF, CAMPATH1-antigen, CD22, CA-125, HLA-DR, Hodgkin-lymphoma or mucin-1, but are not limited thereto.

The term "viral antigen" refers to any viral component having antigenic properties, i.e. being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

The term "disease-associated antigen" is used in it broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen may therefore be used for therapeutic purposes. Disease-associated antigens are preferably associated with infection by microbes, typically microbial antigens, or associated with cancer, typically tumors.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

The term "disease involving an antigen" refers to any disease which implicates an antigen, e.g. a disease which is characterized by the presence of an antigen. The disease involving an antigen can be an infectious disease, an autoimmune disease, or a cancer disease or simply cancer. As mentioned above, the antigen may be a disease-associated antigen, such as a tumor-associated antigen, a viral antigen, or a bacterial antigen.

The term "infectious disease" refers to any disease which can be transmitted from individual to individual or from organism to organism, and is caused by a microbial agent (e.g. common cold). Infectious diseases are known in the art and include, for example, a viral disease, a bacterial disease, or a parasitic disease, which diseases are caused by a virus, a bacterium, and a parasite, respectively. In this regard, the infectious disease can be, for example, hepatitis, sexually transmitted diseases (e.g. *chlamydia* or gonorrhea), tuberculosis, HIV/acquired immune deficiency syndrome (AIDS), diphtheria, hepatitis B, hepatitis C, cholera, severe acute respiratory syndrome (SARS), the bird flu, and influenza.

The term "autoimmune disease" refers to any disease in which the body produces an immunogenic (i.e. immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases.

The term "immune response" relates to a reaction of the immune system such as to immunogenic organisms, such as bacteria or viruses, cells or substances. The term "immune response" includes the innate immune response and the adaptive immune response. Preferably, the immune response is related to an activation of immune cells, an induction of cytokine biosynthesis and/or antibody production.

It is preferred that the immune response induced by the particles of the present invention comprises the steps of activation of antigen presenting cells, such as dendritic cells and/or macrophages, presentation of an antigen or fragment thereof by said antigen presenting cells and activation of cytotoxic T cells due to this presentation.

The term "immunologically active compound" relates to any compound altering an immune response, preferably by inducing and/or suppressing maturation of immune cells, inducing and/or suppressing cytokine biosynthesis, and/or altering humoral immunity by stimulating antibody production by B cells. Immunologically active compounds possess potent immunostimulating activity including, but not limited to, antiviral and antitumor activity, and can also down-regulate other aspects of the immune response, for example shifting the immune response away from a TH2 immune response, which is useful for treating a wide range of TH2 mediated diseases Immunologically active compounds can be useful as vaccine adjuvants. In one embodiment, the RNA in the particles of the present invention encodes an immunologically active compound. Said compound preferably does not encode an antigen.

The term "immune cells" refers to cells of the immune system involved in defending the body of an individual. The term "immune cells" encompasses specific types of immune cells and their precursors including leucocytes comprising macrophages, monocytes (precursors of macrophages), granulocytes such as neutrophils, eosinophils and basophils, dendritic cells, mast cells, and lymphocytes such as B cells, T cells and natural killer (NK) cells. Macrophages, monocytes (precursors of macrophages), neutrophils, dendritic cells, and mast cells are phagocytic cells.

The term "phagocytic cells" refers to cells that protect the body of an individual by ingesting (phagocytosing) harmful foreign particles, bacteria, and dead or dying cells.

The term "macrophage" refers to a subgroup of phagocytic cells produced by the differentiation of monocytes. Macrophages which are activated by inflammation, immune cytokines or microbial products nonspecifically engulf and kill foreign pathogens within the macrophage by hydrolytic and oxidative attack resulting in degradation of the pathogen. Peptides from degraded proteins are displayed on the macrophage cell surface where they can be recognized by T cells, and they can directly interact with antibodies on the B cell surface, resulting in T and B cell activation and further stimulation of the immune response. Macrophages belong to the class of antigen presenting cells. Preferably, the macrophages are splenic macrophages.

The term "dendritic cell" (DC) refers to another subtype of phagocytic cells belonging to the class of antigen presenting cells. Preferably, dendritic cells are derived from hematopoietic bone marrow progenitor cells. These progenitor cells initially transform into immature dendritic cells. These immature cells are characterized by high phagocytic activity and low T cell activation potential. Immature dendritic cells constantly sample the surrounding environment for pathogens such as viruses and bacteria. Once they have come into contact with a presentable antigen, they become activated into mature dendritic cells and begin to migrate to the spleen or to the lymph node. Immature dendritic cells phagocytose pathogens and degrade their proteins into small pieces and upon maturation present those fragments at their cell surface using MHC molecules. Simultaneously, they upregulate cell-surface receptors that act as co-receptors in T cell activation such as CD80, CD86, and CD40 greatly enhancing their ability to activate T cells. They also upregulate CCR7, a chemotactic receptor that induces the dendritic cell to travel through the blood stream to the spleen or through the lymphatic system to a lymph node. Here they act as antigen-presenting cells and activate helper T cells and killer T cells as well as B cells by presenting them antigens, alongside non-antigen specific co-stimulatory signals. Thus, dendritic cells can actively induce a T cell- or B cell-related immune response. Preferably, the dendritic cells are splenic dendritic cells.

The term "antigen presenting cell" (APC) is a cell of a variety of cells capable of displaying, acquiring, and/or presenting at least one antigen or antigenic fragment on (or at) its cell surface. Antigen-presenting cells can be distinguished in professional antigen presenting cells and non-professional antigen presenting cells.

The term "professional antigen presenting cells" relates to antigen presenting cells which constitutively express the Major Histocompatibility Complex class II (MHC class II) molecules required for interaction with naive T cells. If a T cell interacts with the MHC class II molecule complex on the membrane of the antigen presenting cell, the antigen presenting cell produces a co-stimulatory molecule inducing activation of the T cell. Professional antigen presenting cells comprise dendritic cells and macrophages.

The term "non-professional antigen presenting cells" relates to antigen presenting cells which do not constitutively express MHC class II molecules, but upon stimulation by certain cytokines such as interferon-gamma. Exemplary, non-professional antigen presenting cells include fibroblasts, thymic epithelial cells, thyroid epithelial cells, glial cells, pancreatic beta cells or vascular endothelial cells.

The term "maturation" is defined herein as the action of immature highly phagocytic dendritic cells and macrophages resulting in phenotypic and/or functional modifications of these cells. Especially, in dendritic cells, the associated phenotypic modification is represented by an increase of CD40, CD80, CD86, CD83, MHC class I and II molecule cell surface expression and/or a decrease of CD 14 molecule cell surface expression. The functional changes may be the loss of phagocytic properties, the acquisition of migration abilities, an increased allogeneic T cell stimulation efficiency and changes in the cytokine and chemokine expression profile, and particularly an increased IL-12 secretion. The IL-12 production by DCs is critical for their in vivo function, since this cytokine has been shown to generate a polarization of the immune response towards the Th1 pathway in vivo. A Th1 type immune response is considered as immune response involving stimulation of antigen specific T lymphocytes CD8+, whereas a Th2 type immune response involves rather a stimulation of antibody response and eventually unresponsiveness of the cytotoxic lymphocytes to an antigen.

If, according to the present invention, it is desired to induce or enhance an immune response by using particles as described herein, the immune response may be triggered or enhanced by the therapeutically effective compound retained within the particles. For example, the therapeutically effective compound may stimulate certain immune cells such as T cells. Preferably, said T cells are γδ T cells, more preferably vγ9Vδ2 T cells. Alternatively or additionally, the immune response may be triggered or enhanced by the RNA bound to the cationic lipid in the particles. For example, proteins or peptides encoded by the RNAs or procession products thereof may be presented by major histocompatibility complex (MHC) proteins expressed on antigen presenting cells. The MHC peptide complex can then be recognized by immune cells such as T cells or B cells leading to their activation.

The terms "T-cells" or "T lymphocytes" relate to types of lymphocytes that play a central role in cell-mediated immunity. T-cells or T lymphocytes can be distinguished from other lymphocytes, such as B cells and natural killer (NK) cells, by the presence of a T cell receptor (TCR) on the cell surface. They do not have antigen presenting properties (but rather, requiring B cells or NK cells for its antigen-presenting property). They are called T cells because they mature in the thymus. T cells are capable of recognizing an antigen when displayed on the surface of antigen presenting cells or matrix together with one or more MHC molecules or one or more non-classical MHC molecules.

The term "γδ T cells" (gamma delta T cells) relates to a subset of T cells that possess a distinct T cell receptor (TCR) on their surface. A majority of T cells have a TCR composed of two glycoprotein chains called α- and β-TCR chains. In contrast, in γδ cells, the TCR is made up of one γ-chain and one δ-chain. This group of T cells is usually much less common than αβ T cells. Human γδ T cells play an important role in stress-surveillance responses like infectious diseases and autoimmunity. Transformation-induced changes in tumors are also suggested to cause stress-surveillance responses mediated by γδ T cells and enhance antitumor immunity. Importantly, after antigen engagement, activated γδ T cells at lesional sites provide cytokines (e.g. INFγ, TNFα) and/or chemokines mediating recruitment of other effector cells and show immediate effector functions such as cytotoxicity (via death receptor and cytolytic granules pathways) and ADCC.

The majority of γδ T cells in peripheral blood express the Vγ9Vδ2 T cell receptor (TCRγδ). The term "Vγ9/Vδ2 T cells" relates to cells which constitute the major γδ T cell population in human peripheral blood. Vγ9Vδ2 T cells are unique to humans and primates and are assumed to play an early and essential role in sensing "danger" by invading pathogens as they expand dramatically in many acute infections and may exceed all other lymphocytes within a few days, e.g. in tuberculosis, *salmonellosis*, ehrlichiosis, brucellosis, tularemia, listeriosis, toxoplasmosis, and malaria.

γδ T cells respond to small non-peptidic phosphorylated antigens (phosphoantigens) such as pyrophosphates synthesized in bacteria and isopentenyl pyrophosphate (IPP) produced in mammalian cells through the mevalonate pathway. Whereas IPP production in normal cells is not sufficient for activation of γδ T cells, dysregulation of the mevalonate pathway in tumor cells leads to accumulation of IPP and γδ T cell activation. IPPs can also be therapeutically increased by aminobisphosphonates, which inhibit the mevalonate pathway enzyme farnesyl pyrophosphate synthase (FPPS). Among others, zoledronic acid (ZA, zoledronate, Zometa™, Novartis) represents such an aminobisphosphonate, which is already clinically administered to patients for the treatment of osteoporosis and metastasic bone disease. Upon treatment of PBMCs in vitro, ZA is taken up especially by monocytes. IPP accumulates in the monocytes and they differentiate to antigen-presenting cells stimulating development of γδ T cells, In this setting, the addition of interleukin-2 (IL-2) is preferred as growth and survival factor for activated γδ T cells. Finally, certain alkylated amines have been described to activate Vγ9Vδ2 T cells in vitro, however only at millimolar concentrations.

According to the invention, the term "agent stimulating γδ T cells" relates to compounds stimulating development of γδ T cells, in particular Vγ9Vδ2 T cells, in vitro and/or in vivo, in particular by inducing activation and expansion of γδ T cells. Preferably, the term relates to compounds which in vitro and/or in vivo increase isopentenyl pyrophosphate (IPP) produced in mammalian cells, preferably by inhibiting the mevalonate pathway enzyme farnesyl pyrophosphate synthase (FPPS).

One particular group of compounds stimulating γδ T cells are bisphosphonates, in particular nitrogen-containing bisphosphonates (N-bisphosphonates; aminobisphosphonates). According to the invention, zoledronic acid (INN) or zoledronate (marketed by Novartis under the trade names Zometa, Zomera, Aclasta and Reclast) is a particularly preferred bisphosphonate. Zometa is used to prevent skeletal fractures in patients with cancers such as multiple myeloma and prostate cancer, as well as for treating osteoporosis. It can also be used to treat hypercalcemia of malignancy and can be helpful for treating pain from bone metastases.

The terms "stimulating T cells" or "stimulation of T cells" refer to the induction or activation of a T cell response by a primary signal, such as by the interaction with an antigen-MHC class II complex through the T cell antigen receptor. The term also includes the co-stimulation of T cells, such as through cytokines (e.g. CD80 or CD86 proteins). A T cell is activated if it has received a primary signaling event which initiates an immune response by the T cell.

The term "priming T cells" refers to the induction of a first contact of the T cell with its specific antigen (e.g. by dendritic cells presenting the antigen to T cells), which causes the differentiation of the T cell into an effector T cell (e.g. a cytotoxic T cell or a T helper cell).

The terms "expanding T cells" or "expansion of T cells" refer to the increase of the number of T cells, preferably T cells specifically recognizing an antigen. It is preferred, that the number of T cells specifically recognizing an antigen, e.g. an antigen encoded from the RNA decorating the particle of the present invention, or a procession product of the antigen increases. The antigen or procession product of the antigen is preferably presented in the context of MHC molecules, such as on the surface of antigen presenting cells like dendritic cells or macrophages.

The term "immunotherapy" relates to the treatment of a disease or condition by inducing, enhancing, or suppressing an immune response Immunotherapies designed to elicit or amplify an immune response are classified as activation immunotherapies, while immunotherapies that reduce or suppress an immune response are classified as suppression immunotherapies. The term "immunotherapy" includes antigen immunization or antigen vaccination, or tumor immunization or tumor vaccination. The term "immunotherapy" also relates to the manipulation of immune responses such that inappropriate immune responses are modulated into more appropriate ones in the context of autoimmune diseases such as rheumatoid arthritis, allergies, diabetes or multiple sclerosis.

The terms "immunization" or "vaccination" describe the process of administering an antigen to an individual with the purpose of inducing an immune response, for example, for therapeutic or prophylactic reasons.

The term "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "protect", "prevent", "prophylactic", "preventive", or "protective" relate to the prevention and/or treatment of the occurrence and/or the propagation of a disease, e.g. tumor, in an individual. For example, a prophylactic administration of an immunotherapy, e.g. by administering the pharmaceutical composition of the present invention, can protect the receiving individual from the development of a tumor. For example, a therapeutic administration of an immunotherapy, e.g. by administering the pharmaceutical composition of the present invention, can stop the development of a disease, e.g. lead to the inhibition of the progress/growth of a tumor. This comprises the deceleration of the progress/growth of the tumor, in particular a disruption of the progression of the tumor, which preferably leads to elimination of the tumor. A therapeutic administration of an immunotherapy may protect the individual, for example, from the dissemination or metastasis of existing tumors.

The term "water-soluble compound" refers to any compound which is able to dissolve in water. Generally, the underlying solvation arises because of the attraction between positive and negative charges of the compound with the partially negative and partially positive charges of the $H_2O$-molecules, respectively. Compounds which dissolve in water are also termed "hydrophilic" ("water-loving"). Water solubility ($S_W$), also known as aqueous solubility, is the maximum amount of a substance that can dissolve in water at equilibrium at a given temperature and pressure. Generally, the limited amount is given by the solubility product. Following the definition of solubility in the European Pharmacopoeia, "sparingly soluble" means that the approximate volume of solvent in millilitres per gram of solute is from 30 to 100 (at a temperature between 15° C. and 25° C.), "soluble" means that the approximate volume of solvent in millilitres per gram of solute is from 10 to 30 (at a temperature between 15° C. and 25° C.), "freely soluble" means that the approximate volume of solvent in millilitres per gram of solute is from 1 to 10 (at a temperature between 15° C. and 25° C.), and "very soluble" means that the approximate volume of solvent in millilitres per gram of solute is less than 1 (at a temperature between 15° C. and 25° C.). For purposes of the present invention, RNA is considered a hydrophilic compound.

The term "small molecule compound" refers here to a molecule with low molecular mass that can act to affect biological processes. Small molecules can include any number of therapeutic agents presently known and used, or can be small molecules synthesized in a library of such molecules for the purpose of screening for biological function(s). The small molecule compound usually has a molecular mass equal to or less than 1,000 Da, such as equal to or less than 500 Da. The small molecule compound preferably serves as regulating molecule of biological processes such as an enzyme substrate, an antagonist, or an allosterically activating or an allosterically inhibiting molecule. It is preferred, that the molecule is capable of binding to another molecule, such as a protein, nucleic acid or polysaccharide, and acting as an effector, altering the activity of the other molecule.

The terms "individual" and "subject" are used herein interchangeably. They refer to a human or another mammal (e.g. mouse, rat, rabbit, dog, cat, cattle, swine, sheep, horse or primate) that can be afflicted with or is susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In preferred embodiments of the present invention, the "individual" or "subject" is a "patient".

The term "patient" means an individual or subject for treatment, in particular a diseased individual or subject, including human beings, non-human primates or another animals, in particular mammals such as cows, horses, pigs, sheeps, goats, dogs, cats or rodents such as mice and rats. In particularly preferred embodiments of the present invention, the patient is a human being.

The particles of the present invention may be administered in the form of any suitable pharmaceutical composition. The term "pharmaceutical composition" relates to a formulation comprising a therapeutically effective agent or a salt thereof, preferably together with pharmaceutical excipients such as buffers, preservatives and tonicity modifiers. Said pharmaceutical composition is useful for treating, preventing, or reducing the severity of a disease or disorder by administration of said pharmaceutical composition to an individual. A pharmaceutical composition is also known in the art as a pharmaceutical formulation. The pharmaceutical composition can be administered locally or systemically, preferably systemically. In the context of the present invention, the pharmaceutical composition comprises the particle of the invention. This particle is therapeutically effective.

The term "systemic administration" refers to the administration of a therapeutically effective agent such that the agent becomes widely distributed in the body of an individual in significant amounts and develops a biological effect. For example, the agent may develop its desired effect in the blood and/or reaches its desired site of action via the vascular system. Typical systemic routes of administration include administration by introducing the agent directly into the vascular system or oral, pulmonary, or intramuscular administration wherein the agent is adsorbed, enters the vascular system, and is carried to one or more desired site(s) of action via the blood.

According to the present invention, it is preferred that the systemic administration is by parenteral administration. The term "parenteral administration" refers to administration of a therapeutically effective agent such that the agent does not pass the intestine. The term "parenteral administration" includes intravenous administration, subcutaneous administration, intradermal administration or intraarterial administration but is not limited thereto.

The pharmaceutical compositions of the present invention preferably comprise at least one adjuvant. The term "adjuvant" relates to compounds, which when administered in combination with an antigen or antigen peptide to an individual, prolongs or enhances or accelerates an immune response. It is assumed that adjuvants exert their biological activity by one or more mechanisms, including an increase of the surface of the antigen, a prolongation of the retention of the antigen in the body, a retardation of the antigen release, targeting of the antigen to macrophages, increase of the uptake of the antigen, enhancement of antigen processing, stimulation of cytokine release, stimulation and activation of immune cells such as B cells, macrophages, dendritic cells, T cells and unspecific activation of immune cells. Adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples for adjuvants include saponins, incomplete Freund's adjuvants, complete Freund's adjuvants, tocopherol or alum, but are not limited thereto.

The pharmaceutical composition according to the present invention is generally applied in a "pharmaceutically effective amount" and in "a pharmaceutically acceptable preparation".

The term "pharmaceutically acceptable" refers to the non-toxicity of a material which does not interact with the action of the active component of the pharmaceutical composition.

The term "pharmaceutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the particles or compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the particles or compositions described herein may depend on various of such parameters. In the case that a reaction in a patient is insufficient with an initial dose, higher doses (or effectively higher doses achieved by a different, more localized route of administration) may be used.

The pharmaceutical compositions of the present invention may contain salts, buffers, preserving agents, carriers and optionally other therapeutic agents. Preferably, the pharmaceutical compositions of the present invention comprise one or more pharmaceutically acceptable carriers, diluents and/or excipients.

The term "excipient" is intended to indicate all substances in a pharmaceutical composition which are not active ingredients such as binders, lubricants, thickeners, surface active agents, preservatives, emulsifiers, buffers, flavoring agents, or colorants.

The term "diluent" relates a diluting and/or thinning agent. Moreover, the term "diluent" includes any one or more of fluid, liquid or solid suspension and/or mixing media.

The term "carrier" relates to one or more compatible solid or liquid fillers or diluents, which are suitable for an administration to a human. The term "carrier" relates to a natural or synthetic organic or inorganic component which is combined with an active component in order to facilitate the application of the active component. Preferably, carrier components are sterile liquids such as water or oils, including those which are derived from mineral oil, animals, or plants, such as peanut oil, soy bean oil, sesame oil, sunflower oil, etc. Salt solutions and aqueous dextrose and glycerin solutions may also be used as aqueous carrier compounds.

Pharmaceutically acceptable carriers or diluents for therapeutic use are well known in the pharmaceutical art, and are described, for example, in Remington's Pharmaceutical Sciences, Mack Publishing Co. (A. R Gennaro edit. 1985). Examples of suitable carriers include, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Examples of suitable diluents include ethanol, glycerol and water.

Pharmaceutical carriers, excipients or diluents can be selected with regard to the intended route of administration and standard pharmaceutical practice. The pharmaceutical compositions of the present invention may comprise as, or in addition to, the carrier(s), excipient(s) or diluent(s) any suitable binder(s), lubricant(s), suspending agent(s), coating agent(s), and/or solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

The terms "reducing" or "inhibiting" or similar phrases relate to the ability to cause an overall decrease, preferably of at least 5%, at least 10%, at least 20%, at least 30%, at least 40%, at least 50%, at least 80%, or at least 100% in the level, e.g. expression level, particularly compared to a control. The terms "reduce" or "inhibit" or similar phrases include a complete or essentially complete reduction or inhibition, i.e. a reduction or inhibition to zero or essentially zero, particularly compared to a control.

The terms "increasing" or "enhancing" or similar phrases relate to the ability to cause an overall increase or enhancement, preferably of at least 5%, at least 10%, at least 20%, at least 30%, at least 40%, at least 50%, at least 80%, or at least 100% in the level, e.g. expression level, particularly compared to a control.

The term "RNA accumulation" refers to the enrichment of RNA in its broadest sense. Preferably, the enrichment is a local enrichment in a body, organ, tissue, cell type, cell organelles or cell compartment. The term "RNA accumulation" preferably relates to a concentration increase of at least 10%, at least 20%, at least 30%, at least 40%, at least 50%, at least 80%, or at least 100%. According to the present invention, the term "RNA accumulation" can mean a concentration increase of the RNA over time in an individual, organ, tissue, cell type, cell organelle or cell compartment (e.g. change of RNA concentration before and after treatment) or can refer to concentration differences between different individuals, organs, tissues, cell-types, cell organelles or cell compartments (e.g. RNA concentration difference between lung and spleen).

It is preferred in one embodiment that the RNA in the particles of the present invention, after systemic administration, is delivered to the spleen and/or is expressed in the spleen.

In one embodiment, the particles of the present invention are delivered to the spleen for activating splenic antigen presenting cells. Thus, it is preferred that after systemic administration of the particles of the present invention RNA delivery and/or RNA expression in antigen presenting cells occurs. Antigen presenting cells are preferably professional antigen presenting cells or non-professional antigen presenting cells. More preferably, the professional antigen presenting cells are dendritic cells and/or macrophages, even more preferably splenic dendritic cells and/or splenic macrophages.

In one preferred embodiment, the systemic administration of the particles of the present invention results in an increase of the expression of at least one maturation marker in dendritic cells and/or macrophages such as splenic dendritic cells and/or splenic macrophages. Preferably, the maturation marker is selected from the group consisting of CD40, CD80, CD86, CD83, MHC class I and II molecules such as HLA-DR. More preferably, the maturation marker is selected from the group consisting of CD40, CD86, and MHC class II molecules. Even more preferably, the maturation marker is selected from the group consisting of CD40, CD86, and HLA-DR.

The term "about" means greater or less than the value or range of values stated by 1/10 of the stated values, but is not intended to limit any value or range of values. For instance, a concentration value of about 30% means a concentration between 27% and 33%. Each value or range of values preceded by the term "about" is also intended to encompass the embodiment of the stated absolute value or range of values.

The term "portion" refers to a fraction. With respect to a particular structure, the term "portion thereof" may designate a continuous or a discontinuous fraction thereof. A portion may comprise at least 1%, at least 5%, at least 10%, at least 20%, at least 30%, preferably at least 40%, preferably at least 50%, preferably at least 60%, more preferably at least 70%, even more preferably at least 80%, even more preferably at least 90%, and most preferably 100%.

The agents and compositions provided herein may be used alone or in combination with conventional therapeutic regimens such as surgery, irradiation, chemotherapy and/or bone marrow transplantation (autologous, syngeneic, allogeneic or unrelated).

In particular, treatment of cancer represents a field where combination strategies are especially desirable since frequently the combined action of two, three, four or even more cancer drugs/therapies generates synergistic effects which are considerably stronger than the impact of a monotherapeutic approach. Thus, in another embodiment of the present invention, a cancer treatment using the particles of the invention may be effectively combined with various other drugs. Among those are e.g. combinations with conventional tumor therapies, multi-epitope strategies, additional immunotherapy, and treatment approaches targeting angiogenesis or apoptosis (for review see e.g. Andersen et al. 2008: Cancer treatment: the combination of vaccination with other therapies. Cancer Immunology Immunotherapy, 57(11): 1735-1743.) Sequential administration of different agents may inhibit cancer cell growth at different check points, while other agents may e.g. inhibit neo-angiogenesis, survival of malignant cells or metastases, potentially converting cancer into a chronic disease. The following list provides some non-limiting examples of anti-cancer drugs and therapies which can be used in combination with the present invention:

1. Chemotherapy

Chemotherapy is the standard of care for multiple types of cancer. The most common chemotherapy agents act by killing cells that divide rapidly, one of the main properties of cancer cells. Thus, a combination with conventional chemotherapeutic drugs such as e.g. alkylating agents, antimetabolites, anthracyclines, plant alkaloids, topoisomerase inhibitors, and other antitumour agents which either affect cell division or DNA synthesis may significantly improve the therapeutic effects of the present invention by clearing suppressor cells, reboot of the immune system, by rendering tumor cells more susceptible to immune mediated killing, or by additional activation of cells of the immune system. A synergistic anti-cancer action of chemotherapeutic and vaccination-based immunotherapeutic drugs has been demonstrated in multiple studies (see e.g. Quoix et al. 2011: Therapeutic vaccination with TG4010 and first-line chemotherapy in advanced non-small-cell lung cancer: a controlled phase 2B trial. Lancet Oncol. 12(12): 1125-33; see also Liseth et al. 2010: Combination of intensive chemotherapy and anticancer vaccines in the treatment of human malignancies: the hematological experience. 3 Biomed Biotechnol. 2010: 6920979; see also Hirooka et al 2009: A combination therapy of gemcitabine with immunotherapy for patients with inoperable locally advanced pancreatic cancer. Pancreas 38(3): e69-74). There are hundreds of chemotherapeutic drugs available which are basically suitable for combination therapies. Some (non-limiting) examples of chemotherapeutic drugs which can be combined with the present invention are carboplatin (Paraplatin), cisplatin (Platinol, Platinol-AQ), cyclophosphamide (Cytoxan, Neosar), docetaxel (Taxotere), doxorubicin (Adriamycin), erlotinib (Tarceva), etoposide (VePesid), fluorouracil (5-FU), gemcitabine (Gemzar), imatinib mesylate (Gleevec), irinotecan (Camptosar), methotrexate (Folex, Mexate, Amethopterin), paclitaxel (Taxol, Abraxane), sorafinib (Nexavar), sunitinib (Sutent), topotecan (Hycamtin), vincristine (Oncovin, Vincasar PFS), and vinblastine (Velban).

2. Surgery

Cancer surgery—an operation to remove the tumor—remains the foundation of cancer treatment. Surgery can be combined with other cancer treatments in order to delete any remaining tumor cells. Combining surgical methods with subsequent immunotherapeutic treatment is a promising approach which has been demonstrated countless times.

3. Radiation

Radiation therapy remains an important component of cancer treatment with approximately 50% of all cancer patients receiving radiation therapy during their course of illness. The main goal of radiation therapy is to deprive cancer cells of their multiplication (cell division) potential. The types of radiation used to treat cancer are photons radiation (x-rays and gamma rays) and particle radiations (electron, proton and neutron beams.) There are two ways to deliver the radiation to the location of the cancer. External beam radiation is delivered from outside the body by aiming high-energy rays (photons, protons or particle radiation) to the location of the tumor. Internal radiation or brachytherapy is delivered from inside the body by radioactive sources, sealed in catheters or seeds directly into the tumor site. Radiation therapy techniques which are applicable in combination with the present invention are e.g. fractionation (radiation therapy delivered in a fractionated regime, e.g. daily fractions of 1.5 to 3 Gy given over several weeks), 3D conformal radiotherapy (3DCRT; delivering radiation to the gross tumor volume), intensity modulated radiation therapy (IMRT; computer-controlled intensity modulation of multiple radiation beams), image guided radiotherapy (IGRT; a technique comprising pre-radiotherapy imaging which allows for correction), and stereotactic body radiation therapy (SRBT, delivers very high individual doses of radiation over only a few treatment fractions). For a radiation therapy review see Baskar et al. 2012: Cancer and radiation therapy: current advances and future directions. Int. J Med Sci. 9(3): 193-199.

4. Antibodies

Antibodies (preferably monoclonal antibodies) achieve their therapeutic effect against cancer cells through various mechanisms. They can have direct effects in producing apoptosis or programmed cell death. They can block components of signal transduction pathways such as e.g. growth factor receptors, effectively arresting proliferation of tumor cells. In cells that express monoclonal antibodies, they can bring about anti-idiotype antibody formation. Indirect effects include recruiting cells that have cytotoxicity, such as monocytes and macrophages. This type of antibody-mediated cell kill is called antibody-dependent cell mediated cytotoxicity (ADCC). Antibodies also bind complement, leading to direct cell toxicity, known as complement dependent cytotoxicity (CDC). Combining surgical methods with immunotherapeutic drugs or methods is an successful approach, as e.g. demonstrated in Gadri et al. 2009: Synergistic effect of dendritic cell vaccination and anti-CD20 antibody treatment in the therapy of murine lymphoma. J Immunother. 32(4): 333-40. The following list provides some non-limiting examples of anti-cancer antibodies and potential antibody targets (in brackets) which can be used in combination with the present invention: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Bavituximab (phosphatidylserine), Bectumomab (CD22), Belimumab (BAFF), Bevacizumab (VEGF-A), Bivatuzumab mertansine (CD44 v6), Blinatumomab (CD19), Brentuximab vedotin (CD30 TNFRSF8), Cantuzumab mertansin (mucin CanAg), Cantuzumab ravtansine (MUC1), Capromab pendetide (prostatic carcinoma cells), Carlumab (CNTO888), Catumaxomab (EpCAM, CD3), Cetuximab (EGFR), Citatuzumab bogatox (EpCAM), Cixutumumab (IGF-1 receptor), Claudiximab (Claudin), Clivatuzumab tetraxetan (MUC1), Conatumumab (TRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 ganglioside), Edrecolomab (EpCAM), Elotuzumab (SLAMF7), Enavatuzumab (PDL192), Ensituximab (NPC-1C), Epratuzumab (CD22), Ertumaxomab (HER2/neu, CD3), Etaracizumab (integrin αvβ3), Farletuzumab (folate receptor 1), FBTA05 (CD20), Ficlatuzumab (SCH 900105), Figitumumab (IGF-1 receptor), Flanvotumab (glycoprotein 75), Fresolimumab (TGF-β), Galiximab (CD80), Ganitumab (IGF-I), Gemtuzumab ozogamicin (CD33), Gevokizumab (IL-1β), Girentuximab (carbonic anhydrase 9 (CA-IX)), Glembatumumab vedotin (GPNMB), Ibritumomab tiuxetan (CD20), Icrucumab (VEGFR-1), Igovoma (CA-125), Indatuximab ravtansine (SDC1), Intetumumab (CD51), Inotuzumab ozogamicin (CD22), Ipilimumab (CD152), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL-5), Milatuzumab (CD74), Mitumomab (GD3 ganglioside), Mogamulizumab (CCR4), Moxetumomab pasudotox (CD22), Nacolomab tafenatox (C242 antigen), Naptumomab estafenatox (5T4), Namatumab (RON), Necitumumab (EGFR), Nimotuzumab (EGFR), Nivolumab (IgG4), Ofatumumab (CD20), Olaratumab (PDGF-R α), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzumab (HER2/neu), Pintumomab (adenocarcinoma antigen), Pritumumab (vimentin), Racotumomab (N-glycolylneuraminic acid), Radretumab (fibronectin extra domain-B), Rafivirumab (rabies virus glycoprotein), Ramucirumab (VEGFR2), Rilotumumab (HGF), Rituximab (CD20), Robatumumab (IGF-1 receptor), Samalizumab (CD200), Sibrotuzumab (FAP), Siltuximab (IL-6), Tabalumab (BAFF), Tacatuzumab tetraxetan (alpha-fetoprotein), Taplitumomab paptox (CD19), Tenatumomab (tenascin C), Teprotumumab (CD221), Ticilimumab (CTLA-4), Tigatuzumab (TRAIL-R2), TNX-650 (IL-13), Tositumomab (CD20), Trastuzumab (HER2/neu), TRBS07 (GD2), Tremelimumab (CTLA-4), Tucotuzumab celmoleukin (EpCAM), Ublituximab (MS4A1), Urelumab (4-1BB), Volociximab (integrin α5β1), Votumumab (tumor antigen CTAA16.88), Zalutumumab (EGFR), Zanolimumab (CD4).

5. Cytokines, Chemokines, Costimulatory Molecules, Fusion Proteins

Combined usage of the pharmaceutical compositions of the present invention such as the antigen-coding pharmaceutical compositions of the present invention with cytokines, chemokines, costimulatory molecules and/or fusion proteins thereof to evoke beneficial immune modulation or tumor inhibition effects is another embodiment of the present invention. In order to increase the infiltration of immune cells into the tumor and facilitate the movement of antigen-presenting cells to tumor-draining lymph nodes, various chemokines with C, CC, CXC and CX3C structures might be used. Some of the most promising chemokines are e.g CCR7 and its ligands CCL19 and CCL21, furthermore CCL2, CCL3, CCL5, and CCL16. Other examples are CXCR4, CXCR7 and CXCL12. Furthermore, costimulatory or regulatory molecules such as e.g. B7 ligands (B7.1 and B7.2) are useful. Also useful are other cytokines such as e.g. interleukins especially (e.g. IL-1 to IL17), interferons (e.g. IFNalpha1 to IFNalpha8, IFNalpha10, IFNalpha13, IFNalpha14, IFNalpha16, IFNalpha17, IFNalpha21, IFNbeta1, IFNW, IFNE1 and IFNK), hematopoietic factors, TGFs (e.g. TGF-α, TGF-β, and other members of the TGF family), finally members of the tumor necrosis factor family of receptors and their ligands as well as other stimulatory molecules, comprising but not limited to 4-1BB, 4-1BB-L, CD137, CD137L, CTLA-4GITR, GITRL, Fas, Fas-L, TNFR1, TRAIL-R1, TRAIL-R2, p75NGF-R, DR6, LT.beta.R, RANK, EDAR1, XEDAR, Fn114, Troy/Trade, TAJ, TNFRII, HVEM, CD27, CD30, CD40, 4-1BB, OX40, GITR, GITRL, TACI, BAFF-R, BCMA, RELT, and CD95 (Fas/APO-1), glucocorticoid-induced TNFR-related protein, TNF receptor-related apoptosis-mediating protein (TRAMP) and death receptor-6 (DR6). Especially CD40/CD40L and OX40/OX40L are important targets for combined immunotherapy because of their direct impact on T cell survival and proliferation. For a review see Lechner et al. 2011: Chemokines, costimulatory molecules and fusion proteins for the immunotherapy of solid tumors. Immunotherapy 3 (11), 1317-1340.

6. Bacterial Treatments

Researchers have been using anaerobic bacteria, such as *Clostridium novyi*, to consume the interior of oxygen-poor tumours. These should then die when they come in contact with the tumour's oxygenated sides, meaning they would be harmless to the rest of the body. Another strategy is to use anaerobic bacteria that have been transformed with an enzyme that can convert a non-toxic prodrug into a toxic drug. With the proliferation of the bacteria in the necrotic and hypoxic areas of the tumour, the enzyme is expressed solely in the tumour. Thus, a systemically applied prodrug is metabolised to the toxic drug only in the tumour. This has been demonstrated to be effective with the nonpathogenic anaerobe *Clostridium sporogenes*.

7. Kinase Inhibitors

Another large group of potential targets for complementary cancer therapy comprises kinase inhibitors, because the growth and survival of cancer cells is closely interlocked with the deregulation of kinase activity. To restore normal kinase activity and therefor reduce tumor growth a broad range of inhibitors is in used. The group of targeted kinases comprises receptor tyrosine kinases e.g. BCR-ABL, B-Raf, EGFR, HER-2/ErbB2, IGF-IR, PDGFR-α, PDGFR-β, c-Kit, Flt-4, Flt3, FGFR1, FGFR3, FGFR4, CSF1R, c-Met, RON, c-Ret, ALK, cytoplasmic tyrosine kinases e.g. c-SRC, c-YES, Abl, JAK-2, serine/threonine kinases e.g. ATM, Aurora A & B, CDKs, mTOR, PKCi, PLKs, b-Raf, S6K, STK11/LKB1 and lipid kinases e.g. PI3K, SK1. Small molecule kinase inhibitors are e.g. PHA-739358, Nilotinib, Dasatinib, and PD166326, NSC 743411, Lapatinib (GW-572016), Canertinib (CI-1033), Semaxinib (SU5416), Vatalanib (PTK787/ZK222584), Sutent (SU11248), Sorafenib (BAY 43-9006) and Leflunomide (SU101). For more information see e.g. Zhang et al. 2009: Targeting cancer with small molecule kinase inhibitors. Nature Reviews Cancer 9, 28-39.

8. Toll-Like Receptors

The members of the Toll-like receptor (TLRs) family are an important link between innate and adaptive immunity and the effect of many adjuvants rely on the activation of TLRs. A large number of established vaccines against cancer incorporate ligands for TLRs for boosting vaccine responses. Besides TLR2, TLR3, TLR4 especially TLR7 and TLR 8 have been examined for cancer therapy in passive immunotherapy approaches. The closely related TLR7 and TLR8 contribute to antitumor responses by affecting immune cells, tumor cells, and the tumor microenvironment and may be activated by nucleoside analogue structures. All TLR's have been used as stand-alone immunotherapeutics or cancer vaccine adjuvants and may be synergistically combined with the formulations and methods of the present invention. For more information see van Duin et al. 2005: Triggering TLR signaling in vaccination. Trends in Immunology, 27(1):49-55.

9. Angiogenesis Inhibitors

In addition to therapies which target immune modulatory receptors affected by tumor-mediated escape mechanisms and immune suppression there are therapies which target the tumor environment. Angiogenesis inhibitors prevent the extensive growth of blood vessels (angiogenesis) that tumors require to survive. The angiogenesis promoted by tumor cells to meet their increasing nutrient and oxygen demands for example can be blocked by targeting different molecules. Non-limiting examples of angiogenesis-mediating molecules or angiogenesis inhibitors which may be combined with the present invention are soluble VEGF (VEGF isoforms VEGF121 and VEGF165, receptors VEGFR1, VEGFR2 and co-receptors Neuropilin-1 and Neuropilin-2) 1 and NRP-1, angiopoietin 2, TSP-1 and TSP-2, angiostatin and related molecules, endostatin, vasostatin, calreticulin, platelet factor-4, TIMP and CDAI, Meth-1 and Meth-2, IFN-α, -β and -γ, CXCL10, IL-4, -12 and -18, prothrombin (kringle domain-2), antithrombin III fragment, prolactin, VEGI, SPARC, osteopontin, maspin, canstatin, proliferin-related protein, restin and drugs like e.g. bevacizumab, itraconazole, carboxyamidotriazole, TNP-470, CM101, IFN-α, platelet factor-4, suramin, SU5416, thrombospondin, VEGFR antagonists, angiostatic steroids+heparin, cartilage-derived angiogenesis Inhibitory factor, matrix metalloproteinase inhibitors, 2-methoxyestradiol, tecogalan, tetrathiomolybdate, thalidomide, thrombospondin, prolactinα Vβ3 inhibitors, linomide, tasquinimod, For review see Schoenfeld and Dranoff 2011: Anti-angiogenesis immunotherapy. Hum Vaccin. (9):976-81.

10. Small Molecule Targeted Therapy Drugs

Small molecule targeted therapy drugs are generally inhibitors of enzymatic domains on mutated, overexpressed, or otherwise critical proteins within the cancer cell. Prominent and non-limiting examples are the tyrosine kinase inhibitors imatinib (Gleevec/Glivec) and gefitinib (Iressa). The use of small molecules e.g. sunitinib malate and/or sorafenib tosylate targeting some kinases in combination with vaccines for cancer therapy is also described in previous patent application US2009004213.

11. Virus-Based Vaccines

There are a number of virus-based cancer vaccines available or under development which can be used in a combined therapeutic approach together with the formulations of the present invention. One advantage of the use of such viral vectors is their intrinsic ability to initiate immune responses, with inflammatory reactions occurring as a result of the viral infection creating the danger signal necessary for immune activation. An ideal viral vector should be safe and should not introduce an anti-vector immune response to allow for boosting antitumour specific responses. Recombinant viruses such as vaccinia viruses, herpes simplex viruses, adenoviruses, adeno-associated viruses, retroviruses and avipox viruses have been used in animal tumour models and based on their encouraging results, human clinical trials have been initiated. Especially important virus-based vaccines are virus-like particles (VLPs), small particles that contain certain proteins from the outer coat of a virus. Virus-like particles do not contain any genetic material from the virus and cannot cause an infection but they can be constructed to present tumor antigens on their coat. VLPs can be derived from various viruses such as e.g. the hepatitis B virus or other virus families including Parvoviridae (e.g. adeno-associated virus), Retroviridae (e.g. HIV), and Flaviviridae (e.g. Hepatitis C virus). For a general review see Sorensen and Thompsen 2007: Virus-based immunotherapy of cancer: what do we know and where are we going? APMIS 115(11):1177-93; virus-like particles against cancer are reviewed in Buonaguro et al. 2011: Developments in virus-like particle-based vaccines for infectious diseases and cancer. Expert Rev Vaccines 10(11):1569-83; and in Guinén et al. 2010: Virus-like particles as vaccine antigens and adjuvants: application to chronic disease, cancer immunotherapy and infectious disease preventive strategies. Procedia in Vaccinology 2 (2), 128-133.

12. Multi-Epitope Strategies

The use of multi epitopes shows promising results for vaccination. Fast sequencing technologies combined with intelligent algorithms systems allow the exploitation of the tumor mutanome and may provide multi epitopes for individualized vaccines which can be combined with the present invention. For more information see 2007: Vaccination of metastatic colorectal cancer patients with matured dendritic cells loaded with multiple major histocompatibility complex class I peptides. J Immunother 30: 762-772; furthermore Castle et al. 2012: Exploiting the mutanome for tumor vaccination. Cancer Res 72 (5):1081-91.

13. Adoptive T Cell Transfer

For example, a combination of a tumor antigen vaccination and T cell transfer is described in: Rapoport et al. 2011: Combination immunotherapy using adoptive T-cell transfer and tumor antigen vaccination on the basis of hTERT and survivin after ASCT for myeloma. Blood 117(3):788-97.

14. Peptide-Based Target Therapies

Peptides can bind to cell surface receptors or affected extracellular matrix surrounding the tumor. Radionuclides which are attached to these peptides (e.g. RGDs) eventually kill the cancer cell if the nuclide decays in the vicinity of the cell. Especially oligo- or multimers of these binding motifs are of great interest, since this can lead to enhanced tumor specificity and avidity. For non-limiting examples see Yamada 2011: Peptide-based cancer vaccine therapy for prostate cancer, bladder cancer, and malignant glioma. Nihon Rinsho 69(9): 1657-61.

15. Other Therapies

There are numerous other cancer therapies which can be combined with the present invention in order to create synergistic effects. Non-limiting examples are treatments targeting apoptosis, hyperthermia, hormonal therapy, telomerase therapy, insulin potentiation therapy, gene therapy and photodynamic therapy.

The present invention is described in detail by the figures and examples below, which are used only for illustration purposes and are not meant to be limiting. Owing to the description and the examples, further embodiments which are likewise included in the invention are accessible to the skilled worker.

EXAMPLES

Example 1: Materials and Methods

Preparation of Colloidal Lipid Dispersions Comprising ZA by Ethanol Injection Technique and Further Processing 1,2-di-O-octadecenyl-3-trimethylammonium propane (DOTMA), 1,2-di-(9Z-octadecenoyl)-sn-glycero-3-phosphoethanolamine (DOPE) were purchased from Avanti Polar Lipids (Alabaster, Ala.). Cholesterol (purity 99%) was obtained from Sigma (St. Louis, Mo.). Zoledronic acid was obtained from CHEMOS GmbH (Regenstauf, Germany). RNAses free Phosphate buffer saline, hepes buffer were purchased from Ambion (Darmstadt, Germany). RNAse free water was purchased from B-Braun (Melsungen, Germany). All reagents were of analytical grade. Colloids were prepared by a modified ethanol injection technique according to the following protocol:

1.5 ml of the aqueous solution of zoledronic acid (0.66, 1.33, 2.0, 3.33, 6.67, 10.0, 20 mg/ml) in HEPES buffer 100 mM, pH 4.0, was transferred to 50 ml glass beaker. The beaker was put on a magnetic stirrer and the solution was stirred at 400 rpm using IKA big squid model stirrer (IKA, Königswinter Germany).

0.492 ml of a lipid solution in ethanol (DOTMA/DOPE; 2:1 molar ratio and total lipid concentration 270 and 135 mM for DOTMA and DOPE, respectively) was further diluted with absolute ethanol to 0.666 ml (200 and 100 mM for DOTMA and DOPE, respectively) and injected by a syringe (Syring type: Omnifix®-F 1 ml sterile plastic syringe, B. Braun; Melsungen, Germany, Needle: fine needle with 27G size) into the zoledronic acid solution under stirring.

After lipid injection, the suspension was stirred for 10 minutes.

After 10 minutes, 3 ml of RNAse free water were added to the colloid. The lipid and ZA dispersion was stirred for 20 minutes.

Filtration of the Colloid

The obtained raw dispersion of the colloidal dispersion was passed through a Minisart 0.45 μm CE membrane (Sartorius Stedim Biotech GmbH, Goettingen, Germany).

Dialysis of the Colloid

Dialysis of the filtered colloid to remove the free zoledronic acid and ethanol residue was carried out as follows:

Each 1 ml of the colloid was dialyzed versus 200 ml of PBS by using RNAses free Slide-A-Lyzer 10K Dialysis Cassettes (Thermo Fisher Scientific GmbH, Dreieich, Germany).

The dialysis took place at room temperature for 24 hr and at a stirring speed of 400 rpm. The colloid was recovered in sterile falcon tube for further physicochemical characterizations.

Retention of Zoledronic Acid (ZA) in the Colloid

Retained zoledronic acid was quantified by HPLC. The HPLC system consisted of a G1311B quaternary pump, a G4212B DAD (diode array detector) detector, a G1367E auto-sampler AS Hip, a G1330B column oven thermostat, and a ChemStation for LC revision B.04.02 (Agilent technologies, Colorado, USA). The stationary phase was xSelect CSH (C18) column (150 mm×4.6 mm×3.5 μm) (Waters, Eschborn, Germany). The mobile phase was a mixture of methanol (20%) and phosphate buffer 30 mM (80%) containing 5 mM tetrabutylammonium bromide (TCI Deutschland GmbH, Eschborn, Germany) adjusted to pH 7.2. An inoLab pH 7310P pH-meter (WTW, Weilheim, Germany) was used for pH determination of the mobile phase. The flow rate and the column oven temperature were 1 mL/min and 50° C. The detection wavelength was 215 nm. The injection volume amounted to 25 μl. Free zoledronic acid was determined by using high recovery Ultracel with a regenerated cellulose membrane and 30 KD MWCO (Millipore, Schwalbach/Ts., Germany) and using the following steps:

Removal of any preservatives by filtration of 0.1 M NaOH solution followed by PBS through the membrane.

Transfer of 500 μl of the colloid sample to 0.5 mL Ultracel tubes.

Centrifugation of the sample at 4000×g using 40° fixed angle rotor centrifuge Pico 21 (Thermoscientific, Osterode, Germany) at room temperature for 15 minutes.

Collection of the filtrate in a HPLC glass vial for quantification.

Measurement of zoledronic acid concentration in the filtrate by HPLC as mentioned above.

Retention Efficiency % Calculation

Retention efficiency %=[(Total ZA in dialyzed colloid−Free ZA in dialyzed colloid/Total ZA in dialyzed colloid]×(100).

Formation of LNPs Comprising ZA and RNA

According to the required ratio of cationic lipid/RNA (mole/base), the calculated volume of the ZA/lipid colloid was added to the calculated volume of RNA/PBS. The mixture incubated for at least 15 minutes to form LNPs.

Retention of Zoledronic Acid (ZA) as a Function of Starting ZA Concentration in Colloidal Lipid Dispersions The colloidal lipid dispersion was prepared by the ethanol injection technique as described above. Lipid composition was DOTMA/DOPE in a 2/1 molar ratio. ZA was dissolved in 100 mM HEPES buffer at concentration of 20 mg/ml and the pH adjusted to 4 approx. with 5M NaOH. The lipid concentration was approx. 12 mM. Retained and free zoledronic acid was quantified by HPLC. Free zoledronic acid was determined by using high recovery Ultracel with regenerated cellulose membrane and 30 KD MWCO. The samples were centrifuged at 4000×g using 40° fixed angle rotor centrifuge Pico 21 at room temperature for 15 minutes. The filtrate was collected in a HPLC vial for quantification.

Retention of ZA in LNPs Comprising Zoledronic Acid and RNA

Colloidal lipid dispersions comprising ZA with different molar fractions of lipid were mixed with PBS as a control, RNA, and Triton x100. The lipid composition was DOTMA/DOPE in a 2/1 molar ratio. ZA/lipid dispersions were prepared by mixing a calculated volume of lipid dispersions comprising ZA with the calculated volume of RNA at three different lipid concentrations 2, 4, and 6 mM. The ZA/lipid dispersions and RNA were mixed at 1:1 ratio (v/v). The cationic lipid/RNA charge ratio (mole/base) was 1:2. For PBS and Tritonx100, the calculated RNA volume was replaced by physiological PBS or Triton x100 aqueous solution of 10%. The LNPs comprising ZA and RNA were incubated for 30 minutes at room temperature. Afterwards, they were transferred to 0.5 mL Ultracel tubes previously cleaned from any preservatives by filtration of 0.1 M NaOH solution followed by PBS through the membrane. The samples were centrifuged at 4000×g using 40° fixed angle rotor centrifuge Pico 21 (Thermoscientific, Osterode, Germany) at room temperature for 15 minutes. The filtrate was collected in a HPLC glass vial for quantification. Measurement of zoledronic acid concentration in the filtrate by HPLC as mentioned above.

Cryo-Transmission Electron Microscopy (Cryo-TEM) of LNPs Comprising Zoledronic Acid and RNA Lipid composition of the LNPs was DOTMA/DOPE in a 2:1 molar ratio, they contained RNA at a positive/negative (cationic lipid/RNA nucleotide) ratio of 1.3:2. The final lipid concentration was 0.3 mM. After assembly, the formulations were incubated for 30 minutes at RT before Cryo-TEM measurements. Three µl of the sample have been applied to glow discharged holey carbon support film 3 mm EM grids (copper, 300 mesh, 3.5 micron hole/1 micron film, Quantifoil, Plano, Jena, Germany) Immediately after application, samples have been blotted (1.5 seconds, −1 blot force, single blotting, 90% humidity, 15 degrees Celsius) and frozen in liquid ethane by an automatic plunge freezing system (Vitrobot, Mark II, FEI Company, Eindhoven, The Netherlands). Vitrified samples were stored in liquid nitrogen. Low temperature transfer has been done by a single tilt liquid nitrogen cryo-transfer holder (model 626, Gatan, Pleasanton, USA). A Tecnai F30 microscope (FEI Company, Eindhoven, The Netherlands) tuned to 300 kV acceleration voltage has been used for low dose transmission cryo electron microscopy. Data acquisition has been done at an UltraScan US4000 CCD camera (Gatan, Pleasanton, USA). Pixel sizes have been between 0.15 and 1 nm at the specimen level. Images have been taken by Digital Micrograph software (Gatan, Pleasanton, USA) and are shown without further data processing.

PBMC Cells

Peripheral blood mononuclear cells (PBMCs) were isolated from Buffy Coat donations, drawn from the "Transfusions-Zentrale" of Universitätsmedizin Mainz, by density-centrifugation on a Ficoll-Hypaque density gradient.

After isolation PBMCs were further processed to generate CD14+ mononuclear cells by using CD14 MicroBeads and LS columns (Miltenyi Biotec). Purified CD14+ cells were used to generate conventional immature dendritic cells (iDCs) by 5-day cultivation in standard medium supplemented with GM-CSF (1000 U/mL) and IL-4 (1000 U/mL). CD14-depleted cells, meaning peripheral blood lymphocytes (PBLs), were frozen in liquid nitrogen to be subsequently used in coculture experiments.

The standard medium was RPMI 1640, containing 10% FCS, 2 mM L-glutamine, 100 U/mL and 100 mg/mL.

Flow Cytometry

The following monoclonal antibodies (mAbs) were used: FITC-labled anti-CD83 (HB15e, BD Pharmingen), PE-labled anti-CD86 (IT2.2, BD Pharmingen), APC-labled anti-HLA-DR (G46-6, BD Pharmingen). Viability of cells was always evaluated by using the fixable viability dye eFluor506 (eBioscience).

All flow cytomeric data were acquired using FACSCanto II Flow cytometer (BD Biosciences) and analysed with FlowJo-Software (Tree Star).

γ9δ2 T Cell Proliferation/Expansion

To check the functionality of the retained compound, ZA, the expansion of γ9δ2 T cells was evaluated after cocultivation of ZA-loaded iDCs with cryopreserved PBLs.

For evaluation of ex vivo frequency of γ9δ2 T cells freshly isolated PBMCs were stained with anti-CD3, anti-TCR-Vδ2 mABs and analysed via flow cytometry. Therefore, iDCs have been incubated as indicated for 24 h in standard medium (1×106 cells/mL) containing 5 µM ZA. After loading with ZA, iDCs have been centrifuged and washed with PBS. The coculture of iDCs with PBLs was setup in a ratio of 20 (iDCs): 1 γ9δ2 T cells ex vivo. The medium was supplemented with 10 U/mL IL-2 (Proleukin). After 7-day incubation cells were harvested, washed and stained with anti-CD3, anti-TCR-Vδ2 mABs to evaluate frequency of γ9δ2 T cells and their expansion via flow cytometry. For analysis the expansion rate was determined dividing whole cell amount of γ9δ2 T cells before or after 7-day-cultivation.

RNA Expression

If RNA is still intact when it is bound in LNPs the translation of luciferase-encoding RNA was checked by bioluminescence. Here, 2×10^5 iDCs were seeded in 96-well plate and incubated as indicated for 24 h. After incubation, samples were centrifuged (300 g, 5 min) and supernatants were discarded. For the luciferase assay system (Bright Glo ™, Promega) cell pellets were resuspended in 100 µL standard medium (w/o Pen/Strep) and 100 µL assay-substrate solution was added to each well. The luminescence was measured after 10 min incubation with a luminescence reader (Tecan Infinite M200).

DC Maturation

To evaluate whether formulations/substances lead to a maturation of DCs after incubation, flow cytometry analysis was performed. Therefore, iDCs were seeded in standard medium in a 48-well-Plate (1×10^6 DCs/mL and well) and incubated as indicated over-night, approximately 20 h or for 24 h as well as 48 h. After incubation cells were harvested, washed and stained with anti-CD83, anti-CD86 and anti-HLA-DR mABs. As positive control for maturation a so-called "maturation cocktail" containing following cytokines was used: IL-4 (500 U/mL), GM-CSF (800 U/mL), IL-1ß (10 ng/mL), TNF-α (10 ng/mL), IL-6 (1000 U/mL) and PGE-2 (1 µg/mL). For analysis, the expression of these markers was normalized to negative control, meaning no stimulation (cells only in standard medium).

IPP-Accumulation

It was also evaluated if the LNPs deliver ZA to cytosolic compartment of target cells and subsequently lead to an accumulation of IPP. Therefore, 1×10^6 iDCs/mL (standard medium) were seeded and incubated as indicated in a dose-range of 0.1-125 µM regarding final ZA-concentration in cell culture over-night, approximately 20 h. After incubation, cells of samples were harvested and washed. For extraction, ice-cold acetonitrile (300 µL) and water (200 µL) was added to dry cell pellets. After 5-10 minutes the samples were centrifuged (13.000×g, 1 min.). Then the soluble supernatants were transferred to fresh tubes and dried down in a vacuum centrifuge. Until mass spectrometry analysis of IPP samples were stored at −20° C.

Animals for In Vivo Experiments

Female, 6-12 week old Balb/c mice were obtained from in house breeding of the Zentrale Versuchtiereinrichtung (ZVTE) of the Johannes Gutenberg University Mainz and housed under normal laboratory conditions with circadian light/dark cycles and free access to standard mouse chow and tap water (Approval by the Regional Council's Ethics Committee for Animal Experimentation (Koblenz/Rheinland-Pfalz, Germany, G 12-1-081). Mice were anesthetized with isofluorane and the indicated solutions injected retro-orbital.

RNA Expression Analyzed Via Bioluminescence Imaging

Evaluation of uptake and translation of luciferase (Luc) encoding RNA was performed by non-invasive in vivo bioluminescence imaging using the IVIS Spectrum imaging system (Caliper Life Sciences, Alameda, Calif., USA). 6 h after injection of indicated solutions mice received intraperitoneally an aqueous solution of D-luciferin (150 mg/kg body weight). 5 min later photons emitted were collected for 1 min. Measured bioluminescence signal in regions of interest (ROIs) were quantified and presented as color-scaled images superimposed on grayscale photos of mice using the Living Image software (Caliper Life Sciences). For quantifications, the bioluminescence signal retrieved from the respective organ or tissue was normalized by subtracting background luminescence from a non-signal emitting region.

Splenic DC Maturation Analyzed Via FACS Assay 24 h after injection of indicated solutions, mice were euthanized by cervical dislocation and spleens removed. Splenocytes were obtained by digestion of spleen with collagenase (1 mg/ml; Roche) for 5 min, and subsequently pressing spleens through a 70 µm nylon cell strainer (BD Biosciences, Heidelberg, Germany) using the plunger of a 1 ml syringe. After washing the mesh with PBS, and a centrifugation step for 5 min at 1500 rpm, cells underwent red blood cell lysis (RBC) for 5 min at RT were the pellet was suspended in hypotonically buffer ($KHCO_3/NH_4Cl/EDTA$). And after an additional centrifugation step, cells were suspended in 10 ml PBS/5% FCS. Splenocyte samples were incubated at 4° C. with fluorophore labeled monoclonal antibodies (mAbs) F4-80, CD40, CD86, NK1.1, CD11c, CD8 (all from BD Pharmingen, Heidelberg, Germany) for 30 min, washed with PBS and suspended in 300 µl PBS/5% FCS. Flow cytomeric data of $0.75 \times 10^6$ cells were acquired on a FACSCalibur analytic flow cytometer (BD Biosciences) and analyzed with FlowJo (Tree Star) software.

Test of Isopentenyl Pyrophosphate (IPP) Accumulation 24 h after injection of indicated solutions, mice were sacrificed and indicated tissue (e.g. spleen) collected. The splenocytes were prepared according to the protocol for the splenic DC maturation measurement by FACS assay, without red blood cell lysis. $5 \times 10^6$ splenocytes were extracted using ice-cold acetonitrile (300 µl) and water (200 µl) containing 0.25 nmol/L NaF and $Na_3VO_4$ to prevent degradation of isopentenyl pyrophosphate (IPP) (5 min). After centrifugation at 13.000×g for 1 min, the soluble supernatant extract was transferred to a fresh Eppendorf tube and dried down in a vacuum centrifuge, then stored at −20° C. until mass spectrometry (MS) analysis of IPP.

Analysis of IPP by Mass Spectrometry

The samples were dissolved in 0.28% (v/v) hexylamine in 2% methanol. The molar amounts of IPP in cell extracts were determined by an Agilent 1290 Infinity UHPLC with a 6490 triple quadrupole mass spectrometer (JetStream Technology, negative ion electrospray ionization). IPP is a very hydrophilic compound and therefore the use of hexylamine as an ion-pair agent was necessary to retain this compound into a reversed-phase column. HPLC separation was performed using a Poroshell 120 EC-C18 column (2.1×50 mm, 2.7 µm) and an eluent system consisting of 2.8% (v/v) hexylamine, 1% acetic acid in methanol (1:50 in water, eluent A) and acetonitrile (eluent B). Flow-rate was 0.4 mL/min and injection volume 20 µL. After HPLC separation, negative ion mass spectra for IPP were acquired using a 6490 triple quadrupole mass spectrometer equipped with an electrospray ionization (ESI) source (Agilent Technologies, Colorado, USA). Selected reaction monitoring (SRM) was used for analysis of the compounds in the sample and quantitation was based on characteristic fragment ions. The standard curve was created by using synthetic IPP. The concentrations of the samples were determined using the peak areas of the SRM chromatograms and the standard curve.

Figure 1:
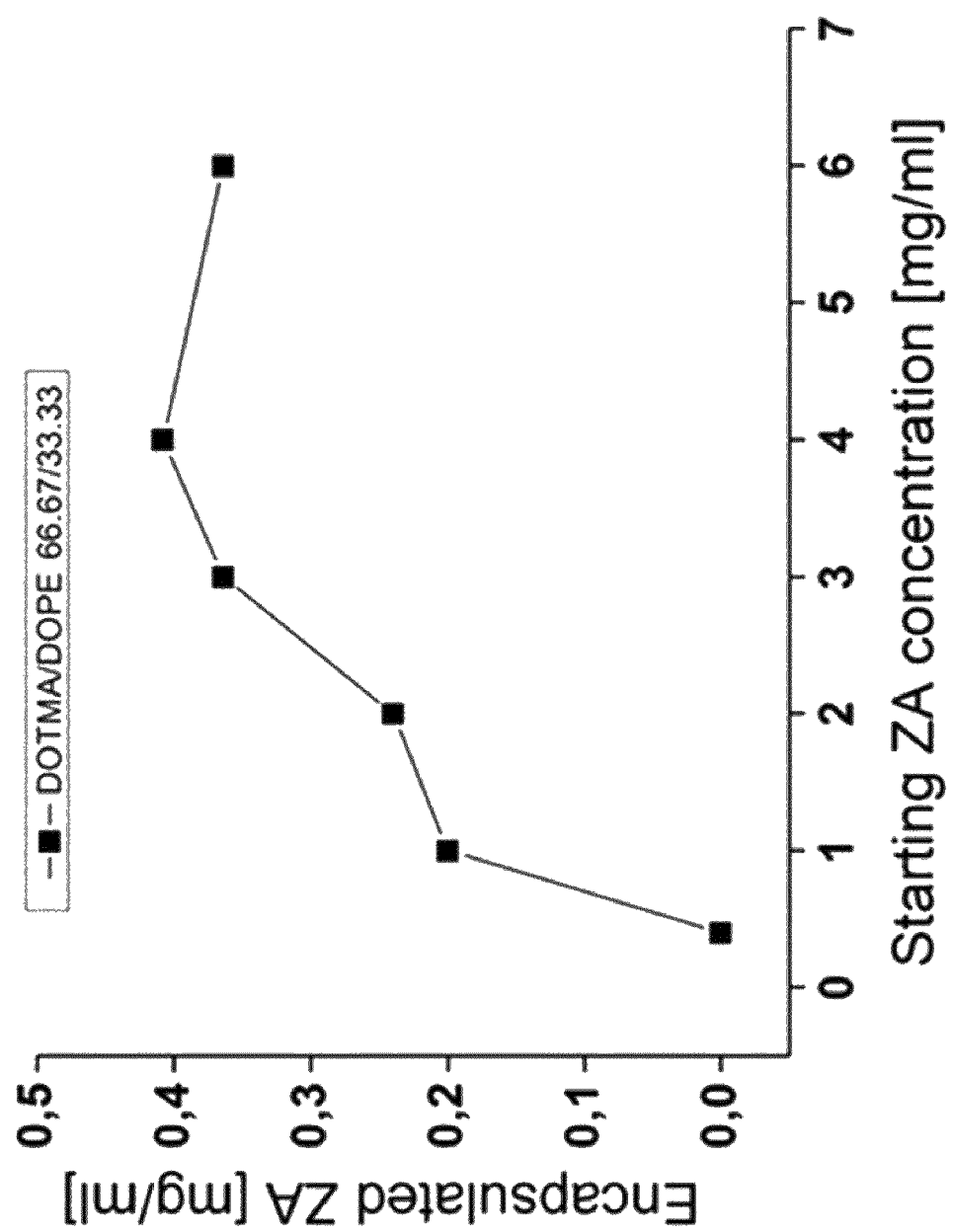
FIG. 1

Example 2: Formation and Characterization of Lipid Particles Comprising a Therapeutically Active Substance and RNA Formation and Retention of ZA in the Colloid Colloidal lipid dispersions comprising ZA were prepared by the ethanol injection method. In this process, an ethanol solution of lipids is rapidly dropped into an aqueous medium through a needle, dispersing the phospholipids throughout the medium and promoting the vesicle formation. In this non-limiting example, the colloid composition was DOTMA/DOPE in a 2 to 1 molar ratio. Colloids were formed when the ethanolic lipid solution was injected into the ZA solution in HEPES buffer pH 4. The total lipid concentration in the aqueous phase was 12 mM while the starting ZA concentrations were 0.4, 1, 2, 3, 4, and 6 mg/ml, respectively. The obtained raw dispersions were filtered through a 0.45 µm CE (Cellulose Ester) membrane. No further filtration or extrusion was performed. Subsequently the colloids were dialyzed in order to remove free ZA. As a result, the absolute amount of ZA retained raises (FIG. 1) with increasing the initial ZA concentrations.

Figure 2:
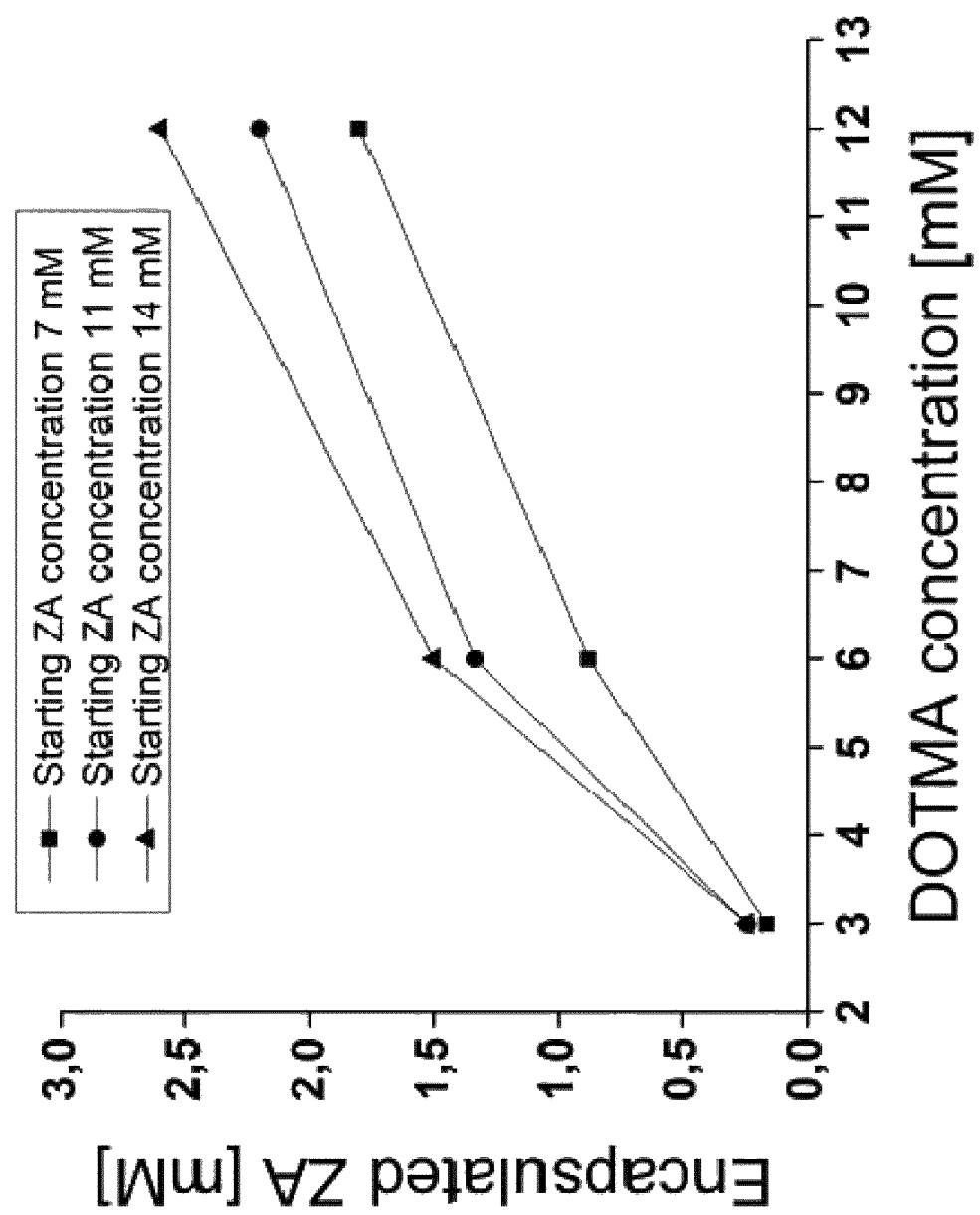
FIG. 2

In another experiment (FIG. 2), the total lipid concentration (DOTMA concentration between 3, 6, and 12 mM) was varied. Here, the absolute amount of retained ZA raises with increasing DOTMA concentrations between 3, 6, and 12 mM.

Figure 3:
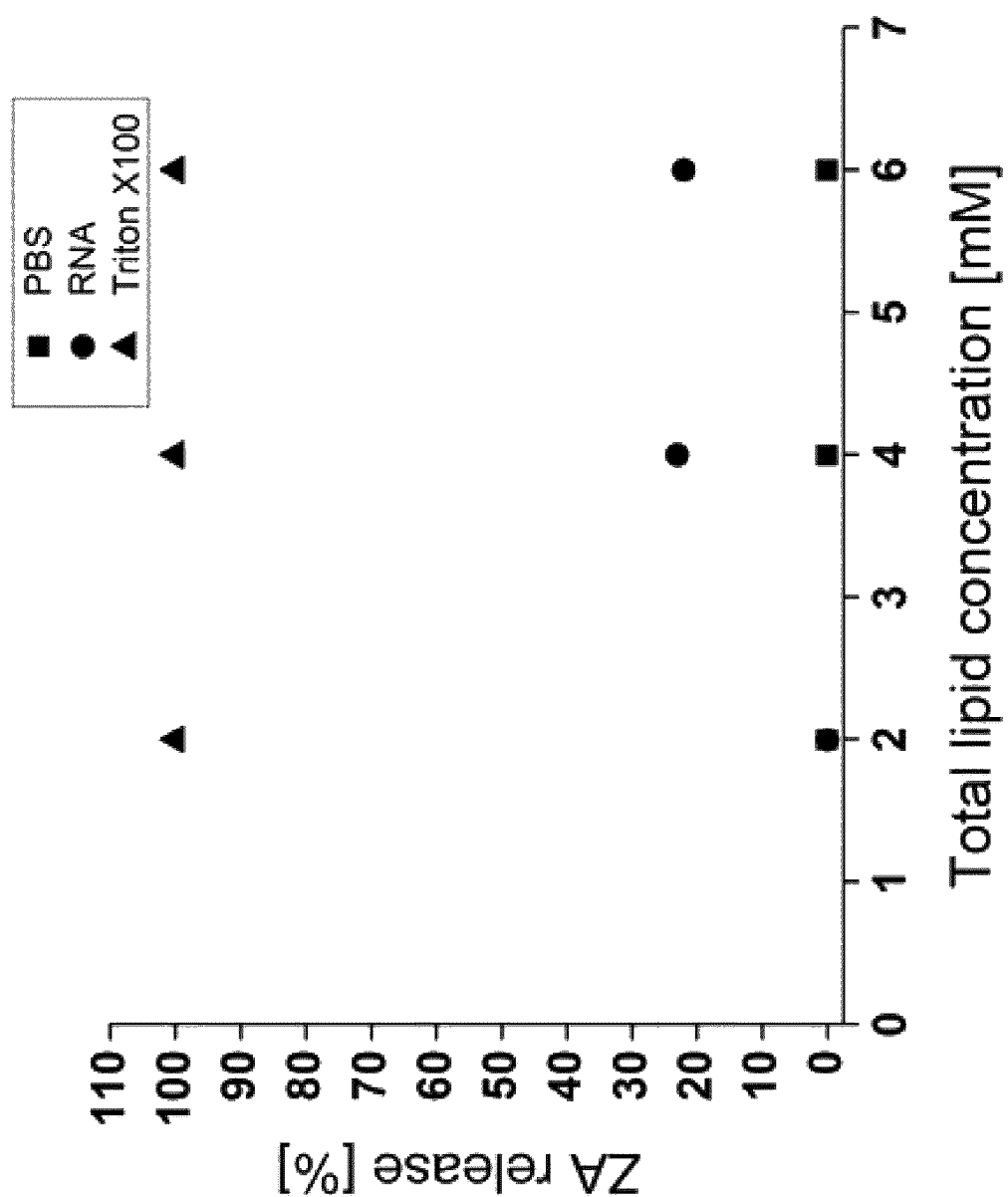
FIG. 3

These colloidal lipid/ZA formulations were used without further processing for the RNA lipoplex formation. From these preparations, the retention of ZA upon addition of RNA was measured. As a negative and positive control for retention, also addition of PBS, and Triton x100 was investigated. On addition of the RNA to the lipid colloid comprising ZA, the ZA was retained by the lipoplexes to a large extent. FIG. 3 indicates that complexation of the ZA colloidal dispersion with RNA leads to retention of the majority of ZA; only 0, 23, and 22% retained ZA was released with respect to total lipid concentrations of 2, 4, and 6 mg/ml, respectively. This finding was confirmed by substitution of RNA with Triton x100 (as a negative control) which led to 100% release of retained ZA. In vivo results, in which IPP accumulation was detected in kidney and bone marrow (showing that ZA was delivered together with the lipoplex to the cytosolic compartment to the target cells) support these results.

Figure 4:
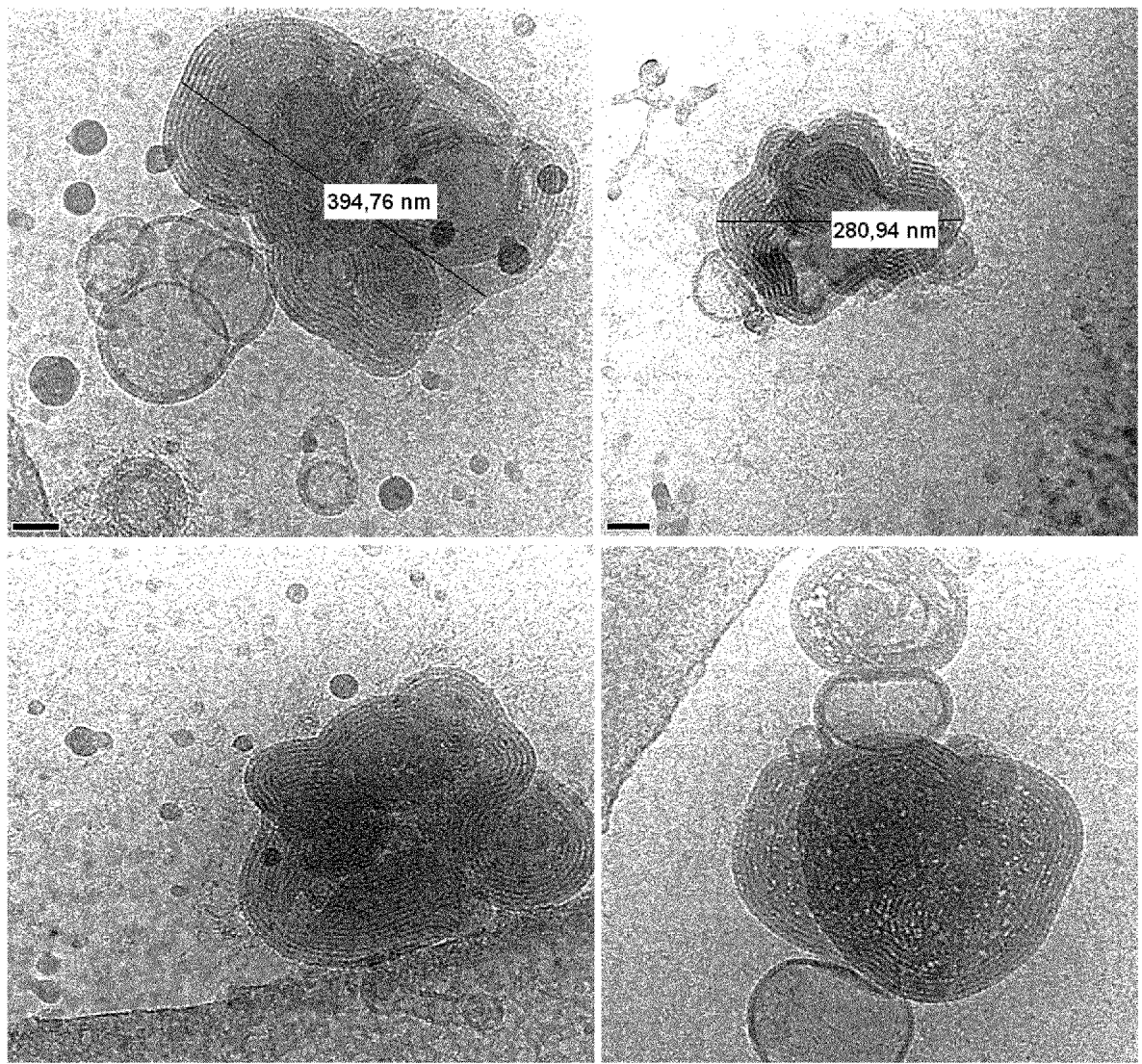
FIG. 4

Cryo-Transmission Electron Microscopy (Cryo-TEM) of LNPs Comprising Zoledronic Acid and RNA Cryo transmission electron microscopy (cryoTEM) imaging was used in order to visualize and determine the size, thickness and microscopic organization of the LNPs comprising RNA and ZA. Inter alia, the LNPs were formed at a cationic lipid/RNA charge ratio of 1.3/2, with a fraction of 0.01 mg/ml ZA, were investigated. After complexing of RNA to cationic ZA colloidal dispersion, the obtained formulation creates organized lamellar structures as shown in FIG. 4. A total size of the LNPs in the range of 200-400 nm was found, where a distinct internal lamellar organization with about 2 to 20 lamellae in a row (analyzing a high number or images) was discernible. The mean number of organized lamellae in a row was between 5 and 15. RNA and the ZA may be retained by this lamellar structure.

Example 3: Functionality of the RNA and the Therapeutically Active Substance in Lipid Particles Comprising a Therapeutically Active Substance and RNA Expression of Luciferase (Luc) In Vitro Transcribed (IVT) RNA in Dendritic Cells (DCs) after Incubation with LNPs Formulations Comprising ZA and RNA It was determined whether RNA coding for a protein such as an antigen and bound to ZA colloidal dispersion was still intact and could be translated into a functional protein such as an antigen in dendritic cells (DCs). RNA encoding the enzyme luciferase (Luc) was incubated with ZA colloidal dispersion. The resulting LNPs comprising luciferase RNA and ZA were incubated with dendritic cells, and luciferase expression was evaluated via luminescence indicating the metabolic rate of luciferin being a substrate for luciferase in counts per seconds (cps). As a result of the luminescence measurement in dendritic cells incubated with LNPs (i.e. luciferase (Luc) RNA bound to ZA colloidal dispersion) or naked RNA (i.e. luciferase RNA not bound to ZA colloidal dispersion), only dendritic cells incubated with LNPs showed a luciferase signal. FIG. 5 demonstrates expression of luciferase IVT-RNA in DCs after incubation with LNP formulations after binding of RNA. In both cases, the transfection efficacy of the RNA was significantly improved which demonstrates that integral RNA is delivered to the target cells by LNPs, where it is taken up and translated into the protein (here luciferase). This indicates that dendritic cells could take up LNPs without destroying the RNA bound to the ZA colloidal dispersion and that the LNPs were stable enough such that the protein (here luciferase) encoding RNA could be translated. Thus, LNPs, and accordingly the particles of the present invention, can be used to induce translation of a protein such as an antigen of choice in dendritic cells. This further indicates that LNPs, and accordingly the particles of the present invention, can be used for immunotherapy e.g. tumor vaccination.

Relative Expression of Maturation Markers in Dendritic Cells after Incubation with LNP Formulations The influence of LNPs (i.e. RNA bound to ZA colloidal dispersion) on the maturation of dendritic cells (Drs) in vitro compared to a positive control (maturation cocktail containing IL-4, GM-CSF, IL-1ß, TNF-α, IL-6 and PGE-2), naked RNA and ZA colloidal dispersion (i.e. zoledronic acid (ZA) entrapped in colloidal dispersion) was determined. The relative expression of the maturation markers CD83, CD86 and HLA-DR was determined using flow cytometry to evaluate the maturation of dendritic cells induced by LNPs. For analysis of the relative expression, the expression of CD83, CD86 and HLA-DR was normalized to the negative control (cells in standard medium). As a result, LNPs evoke a distinct higher expression of CD83, CD86 and HLA-DR compared to naked RNA and ZA colloidal dispersion. Regarding CD86 and HLA-DR, the expression induced by LNPs was comparable with the positive control. The determined increase of the relative expression induced by LNPs was between a factor of 1.5 and 3 for CD83, between a factor of 2.0 and 3.5 for CD86 and between a factor of 1.5 and 2.0 for HLA-DR. This indicates that LNPs induce the maturation of dendritic cells and are, thus, capable of modulating the immune response.

Figure 6:
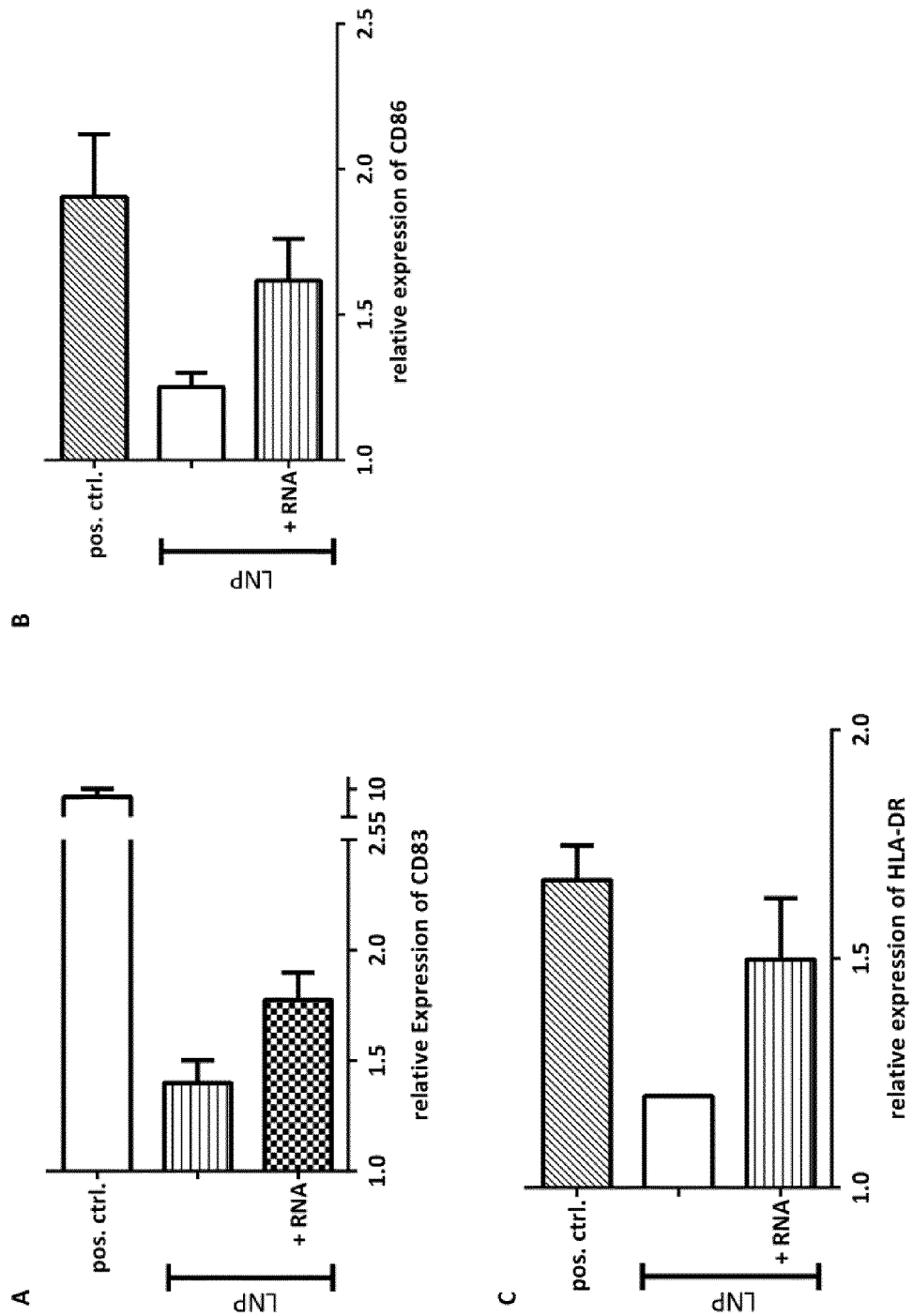
FIG. 6

In FIG. 6, the normalized expression of maturation markers of DCs is shown after administration of the LNPs comprising ZA and RNA together in comparison with the ZA-containing colloid (ZA liposomes) only and a positive control. The relative expression of CD83 (A), CD86 (B) and HLA-DR (C) is shown. Expression data were normalized to no stimulation control. In total, four donors have been tested separately and the mean value is shown including SD. Maturation of DCs could be observed in both cases, as all markers were up-regulated. For the formulation with RNA and ZA together, the effect was even more pronounced.

In FIG. 7, results from measuring the relative expression of maturation markers are given which demonstrate that ZA-containing liposomes lead to maturation of DCs. Dendritic cells have been incubated over 24 h and 48 h with LNPs in 3 different ZA-concentrations (0.5, 5 and 50 µM). Here, the relative expression of maturation markers CD80 (A), CD83 (B), CD6 (C) and HLA-DR (D) is shown. Expression of all maturation markers was upregulated in dendritic cells after incubation with LNPs decorated with IVT-RNA. In total, two donors have been tested separately and the mean value is shown including SD. It could be shown that ZA and RNA containing LNPs lead to a dose-dependent maturation of DCs. This effect on DCs was even more pronounced after 48 h of incubation.

Functionality of Retained Zoledronic Acid (ZA) after Co-Cultivation of Immature Dendritic Cells (iDCs) Incubated with LNPs Formulations and Peripheral Blood Lymphocytes (PBLs)

In order to test whether a retained therapeutic agent was still functional after delivery, the functionality of zoledronic acid (ZA) delivered by the LNPs was evaluated. In particular, the capability of zoledronic acid to induce the expansion of Vγ9Vδ2 T cells was tested (Castella, B., Riganti, C., Fiore, F., Pantaleoni, F., Canepari, M. E., Peola, S., Foglietta, M., Palumbo, A., Bosia, A., Coscia, M., Boccadoro, M., Massaia, M. (2011), The Journal of Immunology 187(4), 1578-90). To investigate the influence of LNPs on the expansion rate of Vγ9Vδ2 cells, zoledronic acid (ZA) loaded immature dendritic cells were co-cultured with peripheral blood lymphocytes containing Vγ9Vδ2 T cells. After seven days of co-culturing, the cells were stained with an anti-CD3 antibody and an anti-TCR-Vδ2 antibody to evaluate the frequency of Vγ9Vδ2 cells and their expansion via flow cytometry. LNPs (i.e. RNA bound to ZA colloidal dispersion, ZA colloidal dispersion (i.e. ZA entrapped in colloidal dispersion) and free zoledronic acid (ZA) cause increase of the percentage of Vγ9δ2 T cells compared to the negative control (no zoledronic acid (ZA)). For analysis, the expansion rate of Vγ9δ2 T cells was determined by dividing the whole cell amount of Vγ9δ2 T cells before the seven day cultivation period by the whole cell amount of Vγ9δ2 T cells after the seven day cultivation period. Treatment with LNPs resulted in an expansion rate of Vγ9δ2 T cells of about 60-fold, ZA colloidal dispersion treatment resulted in an expansion rate of Vγ9δ2 T cells of about 40-fold and free zoledronic acid (ZA) treatment resulted in an expansion rate of Vγ9δ2 T cells of about 15-fold. Thus, LNPs induced expansion of Vγ9δ2 T cells is highly efficient and indicates high functionality of the retained zoledronic acid and good delivery properties of the zoledronic acid.

Example 4: In Vivo Functionality of Lipid Particles Comprising a Therapeutically Active Substance and RNA Application of LNPs Results in Luciferase (Luc) Expression in the Spleen For validation of the in vitro results in vivo, LNPs containing luciferase (Luc)-encoding RNA (corresponding to 20 µg RNA/mouse) were injected into Balb/c mice. The translation of luciferase (Luc) RNA in the LNPs was detected in the presence of luciferin using bioluminescence imaging. Application of LNPs (i.e. luciferase (Luc) RNA bound to ZA colloidal dispersion) resulted in luciferase expression in the spleen. Injection of LNPs (i.e. Luciferase (Luc) RNA bound to ZA colloidal dispersion) induced a significant higher luminescence signal than injection of naked luciferase (Luc) RNA. This indicates that entrapped zoledronic acid (ZA) does not negatively influence RNA uptake and translation in vivo. It rather enhances the expression of protein such as antigen encoding RNA.

Application of LNPs Results in an Upregulation of CD40 and CD86 Expression on Splenic Dentritic Cells (DCs) and Macrophage (mΦ) Cell Population In order to test whether injection of LNPs results in the maturation of splenic dendritic cells and macrophages in vivo, splenocytes of LNPs-treated mices were prepared. Subsequently, the amount of the surface expression of the maturation markers CD40 and CD86 on dendritic cells and macrophages was measured via flow cytometry. An increase of the signal of CD40 and CD86 compared to the negative control (no treatment) was only detected in dendritic cells and in the macrophage cell population in the presence of Luciferase (Luc) or influenza hemagglutinin A (InfHA) RNA bound to zoledronic acid colloidal dispersion (LNPs Luc-RNA or LNPs infHA-RNA) and Luciferase (Luc) or influenza hemagglutinin A (InfHA)

RNA bound to colloidal dispersion (i.e. without ZA) (empty colloidal dispersion+Luc-RNA or empty colloidal dispersion+InfHA-RNA). In contrast thereto, an increase of the signal of CD40 and CD86 compared to the negative control (no treatment) was not detected in dendritic cells and in the macrophage cell population in the presence of ZA colloidal dispersion, empty colloidal dispersion or free RNAs (free Luc-RNA or free InfHA-RNA). These results indicate that treatment with LNPs (i.e. RNA bound to ZA colloidal dispersion) induces maturation of dendritic cells and macrophages in vivo. As luciferase encoding RNA (Luc-RNA) as well as influenza hemagglutinin A encoding RNA (InfHA-RNA) induced maturation of dendritic cells and macrophages, the induction of maturation appears to be independent from the encoded protein. Therefore, any RNA can be bound to the colloidal dispersion in order to induce maturation of splenic dendritic cells and macrophages. This provides a useful method in order to generally induce maturation of splenic dendritic cells and macrophages as well as to introduce an antigen into splenic dendritic cells and macrophages which is specifically useful for vaccination or other immunotherapeutic approaches.

Zoledronic Acid Leads to Accumulation of Isopentenyl Pyrophosphate (IPP) in the Spleen.

After having shown that RNA provided by the LNPs is functionally active, the function of zoledronic acid retained in the LNPs was tested in vivo. Zoledronic acid has been shown to induce accumulation of isopentenyl pyrophosphate (IPP) in various cell lines in vitro and tumor tissue in vivo and could be directly related to improved clinical outcome of cancer of different origin. (Mitrofan, L. M., Pelkonen, J., Mönkkönen, J., (2009), Bone, 45, 1153-60). Thus, IPP accumulation in the spleen was investigated after injection of the LNPs formulations using mass spectrometry. Treatment with zoledronic acid (ZA) colloidal dispersion and luciferase (Luc) RNA bound to ZA colloidal dispersion (Luc-RNA LNPs) resulted in a significant increase of the IPP concentration in the spleen compared to the negative control (no treatment), free luciferase (Luc) RNA (free RNA), empty colloidal dispersion and empty colloidal dispersion bound to luciferase (Luc) encoding RNA. This indicates that zoledronic acid delivered by LNPs is still functional after delivery in vivo. Thus, the in vivo data confirmed the results of the in vitro data, indicating that RNA bound to ZA colloidal dispersion particles can be used for drug delivery. In summary, RNA bound to ZA colloidal dispersion are useful for introduction of protein such as antigen encoding RNA as well as for drug delivery in order to induce/modulate the immune response in an individual.

Example 5: Preparation of Colloidal Lipid Dispersions Comprising ZA by Ethanol Injection Technique and Further Processing

Example 5.1

1,2-di-O-octadecenyl-3-trimethylammonium propane (DOTMA), 1,2-di-(9Z-octadecenoyl)-sn-glycero-3-phosphoethanolamine (DOPE) were purchased from Avanti Polar Lipids (Alabaster, Ala.). Cholesterol (purity 99%) was obtained from Sigma (St. Louis, Mo.). Zoledronic acid was obtained from CHEMOS GmbH (Regenstauf, Germany). RNAses free Phosphate buffer saline was purchased from Ambion (Darmstadt, Germany). RNAse free water was purchased from B-Braun (Melsungen, Germany). All reagents were of analytical grade. Colloids were prepared by a modified ethanol injection technique according to the following protocol:

- In 50 ml glass beaker, 0.25 ml of the aqueous solution of zoledronic acid 20 mg/ml in PBS buffer pH 7.4 added to 1.25 ml of the aqueous solution of sucrose 10%.
- The beaker was put on a magnetic stirrer and the solution was stirred at 400 rpm using IKA big squid model stirrer (IKA, Königswinter Germany).
- 0.600 ml of a lipid solution in ethanol (DOTMA/DOPE; 2:1 molar ratio and total lipid concentration 200 and 100 for DOTMA and DOPE, respectively) was injected by a syringe (Syring type: Omnifix®-F 1 ml sterile plastic syringe, B. Braun; Melsungen, Germany, Needle: fine needle with 27G size) into the zoledronic acid solution under stirring.
- After lipid injection, the suspension was stirred for 10 minutes.

After 10 minutes, 3 ml of RNAse free water were added to the colloid. The lipid and ZA dispersion was stirred for 20 minutes.

Example 5.2

1,2-dioleoyl-3-trimethylammonium-propane (DOTAP), 1,2-di-(9Z-octadecenoyl)-sn-glycero-3-phosphoethanolamine (DOPE) were purchased from Avanti Polar Lipids (Alabaster, Ala.). Cholesterol (purity 99%) was obtained from Sigma (St. Louis, Mo.). Zoledronic acid was obtained from CHEMOS GmbH (Regenstauf, Germany). RNAses free Phosphate buffer saline, hepes buffer were purchased from Ambion (Darmstadt, Germany). RNAse free water was purchased from B-Braun (Melsungen, Germany). All reagents were of analytical grade. Colloids were prepared by a modified ethanol injection technique according to the following protocol:

- 1.5 ml of the aqueous solution of zoledronic acid (0.5, 1, 2.0, 4, 8, 10.0, 20 mg/ml) in HEPES buffer 100 mM, pH 4.0, was transferred to 50 ml glass beaker. The beaker was put on a magnetic stirrer and the solution was stirred at 400 rpm using IKA big squid model stirrer (IKA, Königswinter Germany).
- 0.500 ml of a lipid solution in ethanol (DOTAP/DOPE; 2:1 molar ratio and total lipid concentration 180 and 90 mM for DOTAP and DOPE, respectively) was further diluted with absolute ethanol to 0.600 ml (200 and 100 mM for DOTAP and DOPE, respectively) and injected by a syringe (Syring type: Omnifix®-F 1 ml sterile plastic syringe, B. Braun; Melsungen, Germany, Needle: fine needle with 27G size) into the zoledronic acid solution under stirring.
- After lipid injection, the suspension was stirred for 10 minutes.
- After 10 minutes, 3 ml of RNAse free water were added to the colloid. The lipid and ZA dispersion was stirred for 20 minutes.

Example 5.3

1,2-dioleoyl-sn-glycero-3-ethylphosphocholine (DOEPC), 1,2-dioleoyl-sn-glycero-3-phosphocholine (DOPC) were purchased from Avanti Polar Lipids (Alabaster, Ala.). Cholesterol (purity 99%) was obtained from Sigma (St. Louis, Mo.). Zoledronic acid was obtained from CHEMOS GmbH (Regenstauf, Germany). RNAses free Phosphate buffer saline, hepes buffer were purchased from Ambion (Darmstadt, Germany). RNAse free water was purchased from B-Braun (Melsungen, Germany). Ail reagents were of analytical grade. Colloids were prepared by a modified ethanol injection technique according to the following protocol:

- 1.5 ml of the aqueous solution of zoledronic acid (0.5, 1, 2.0, 4, 8, 10.0, 20 mg/ml) in HEPES buffer 100 mM, pH 4.0, was transferred to 50 ml glass beaker. The beaker was put on a magnetic stirrer and the solution was stirred at 400 rpm using IKA big squid model stirrer (IKA, Königswinter Germany).
- 0.500 ml of a lipid solution in ethanol (DOEPC/DOPC; 2:1 molar ratio and total lipid concentration 200 and 100 mM for DOEPC and DOPC, respectively) was further diluted with absolute ethanol to 0.600 ml (200 and 100 mM for DOEPC and DOPC, respectively) and injected by a syringe (Syring type: Omnifix®-F 1 ml sterile plastic syringe, B. Braun; Melsungen, Germany, Needle: fine needle with 27G size) into the zoledronic acid solution under stirring.
- After lipid injection, the suspension was stirred for 10 minutes.

After 10 minutes, 3 ml of RNAse free water were added to the colloid. The lipid and ZA dispersion was stirred for 20 minutes.

Example 6: Preparation of Colloidal Lipid Dispersions Comprising ZA by Ethanol Injection Technique and Further Processing Example 6.1

1,2-di-O-octadecenyl-3-trimethylammonium propane (DOTMA), 1,2-di-(9Z-octadecenoyl)-sn-glycero-3-phosphoethanolamine (DOPE) were purchased from Avanti Polar Lipids (Alabaster, Ala.). Cholesterol (purity 99%) was obtained from Sigma (St. Louis, Mo.). Zoledronic acid was obtained from CHEMOS GmbH (Regenstauf, Germany). RNAses free Phosphate buffer saline was purchased from Ambion (Darmstadt, Germany). RNAse free water was purchased from B-Braun (Melsungen, Germany). All reagents were of analytical grade. Colloids were prepared by a modified ethanol injection technique according to the following protocol:

- 0.5 ml of the aqueous solution of zoledronic acid 20 mg/ml in HEPES buffer 100 mM, pH 4.0, was mixed with 1 ml HEPES buffer 100 mM, pH 7.0 and transferred to 50 ml glass beaker. The beaker was put on a magnetic stirrer and the solution was stirred at 400 rpm using IKA big squid model stirrer (IKA, Königswinter Germany).
- 0.492 ml of a lipid solution in ethanol (DOTMA/DOPE; 1:1 molar ratio and total lipid concentration 135 and 135 mM for DOTMA and DOPE, respectively) was injected by a syringe (Syring type: Omnifix®-F 1 ml sterile plastic syringe, B. Braun; Melsungen, Germany, Needle: fine needle with 27G size) into the zoledronic acid solution under stirring.
- After lipid injection, the suspension was stirred for 10 minutes.
- After 10 minutes, 3 ml of RNAse free water were added to the colloid. The lipid and ZA dispersion was stirred for 20 minutes.

Filtration of the Colloid

The obtained raw dispersion of the colloidal dispersion was passed through a Minisart 0.45 µm CE membrane (Sartorius Stedim Biotech GmbH, Goettingen, Germany).

Dialysis of the Colloid

Dialysis of the filtered colloid to remove the free zoledronic acid and ethanol residue was carried out as follows:

Each 1 ml of the colloid was dialyzed versus 200 ml of PBS by using RNAses free Slide-A-Lyzer 10K Dialysis Cassettes (Thermo Fisher Scientific GmbH, Dreieich, Germany).

The dialysis took place at room temperature for 24 hr and at a stirring speed of 400 rpm. The colloid was recovered in sterile falcon tube for further physicochemical characterizations.

Retention of Zoledronic Acid (ZA) in the Colloid

Retained zoledronic acid was quantified by HPLC. The HPLC system consisted of a G1311B quaternary pump, a G4212B DAD (diode array detector) detector, a G1367E auto-sampler AS Hip, a G1330B column oven thermostat, and a ChemStation for LC revision B.04.02 (Agilent technologies, Colorado, USA). The stationary phase was xSelect CSH (C18) column (150 mm×4.6 mm×3.5 µm) (Waters, Eschbom, Germany). The mobile phase was a mixture of methanol (20%) and phosphate buffer 30 mM (80%) containing 5 mM tetrabutylammonium bromide (TCI Deutschland GmbH, Eschbom, Germany) adjusted to pH 7.2. An inoLab pH 7310P pH-meter (WTW, Weilheim, Germany) was used for pH determination of the mobile phase. The flow rate and the column oven temperature were 1 mL/min and 50° C. The detection wavelength was 215 nm. The injection volume amounted to 25 Free zoledronic acid was determined by using high recovery Ultracel with a regenerated cellulose membrane and 30 KD MWCO (Millipore, Schwalbach/Ts., Germany) and using the following steps:

Removal of any preservatives by filtration of 0.1 M NaOH solution followed by PBS through the membrane.

Transfer of 500 µl of the colloid sample to 0.5 mL Ultracel tubes.

Centrifugation of the sample at 4000×g using 40° fixed angle rotor centrifuge Pico 21 (Thermoscientific, Osterode, Germany) at room temperature for 15 minutes.

Collection of the filtrate in a HPLC glass vial for quantification.

Measurement of zoledronic acid concentration in the filtrate by HPLC as mentioned above.

Retention Efficiency % Calculation

Retention efficiency %=[(Total ZA in dialyzed colloid−Free ZA in dialyzed colloid/Total ZA in dialyzed colloid]×(100).

Formation of LNPs Comprising ZA and RNA

According to the required ratio of cationic lipid/RNA (mole/base), the calculated volume of the ZA/lipid colloid was added to the calculated volume of RNA/PBS. The mixture incubated for at least 15 minutes to form LNPs.

Retention of Zoledronic Acid (ZA) as a Function of Starting ZA Concentration in Colloidal Lipid Dispersions The colloidal lipid dispersion was prepared by the ethanol injection technique as described above. Lipid composition was DOTMA/DOPE in a 2/1 molar ratio. ZA was dissolved in 100 mM HEPES buffer at concentration of 20 mg/ml and the pH adjusted to 4 approx. with 5M NaOH. The lipid concentration was approx. 12 mM. Retained and free zoledronic acid was quantified by HPLC. Free zoledronic acid was determined by using high recovery Ultracel with regenerated cellulose membrane and 30 KD MWCO. The samples were centrifuged at 4000×g using 40° fixed angle rotor centrifuge Pico 21 at room temperature for 15 minutes. The filtrate was collected in a HPLC vial for quantification.

Retention of ZA in LNPs Comprising Zoledronic Acid and RNA

Colloidal lipid dispersions comprising ZA with different molar fractions of lipid were mixed with PBS as a control, RNA, and Triton x100. The lipid composition was DOTMA/DOPE in a 2/1 molar ratio. ZA/lipid dispersions were prepared by mixing a calculated volume of lipid dispersions comprising ZA with the calculated volume of RNA at three different lipid concentrations 2, 4, and 6 mM. The ZA/lipid dispersions and RNA were mixed at 1:1 ratio (v/v). The cationic lipid/RNA charge ratio (mole/base) was 1:2. For PBS and Tritonx100, the calculated RNA volume was replaced by physiological PBS or Triton x100 aqueous solution of 10%. The LNPs comprising ZA and RNA were incubated for 30 minutes at room temperature. Afterwards, they were transferred to 0.5 mL Ultracel tubes previously cleaned from any preservatives by filtration of 0.1 M NaOH solution followed by PBS through the membrane. The samples were centrifuged at 4000×g using 40° fixed angle rotor centrifuge Pico 21 (Thermoscientific, Osterode, Germany) at room temperature for 15 minutes. The filtrate was collected in a HPLC glass vial for quantification. Measurement of zoledronic acid concentration in the filtrate by HPLC as mentioned above.

Example 6.2

1,2-dioleoyl-3-trimethylammonium-propane (DOTAP), 1,2-di-(9Z-octadecenoyl)-sn-glycero-3-phosphoethanolamine (DOPE) were purchased from Avanti Polar Lipids (Alabaster, Ala.). Cholesterol (purity 99%) was obtained from Sigma (St. Louis, Mo.). Zoledronic acid was obtained from CHEMOS GmbH (Regenstauf, Germany). RNAses free Phosphate buffer saline, hepes buffer were purchased from Ambion (Darmstadt, Germany). RNAse free water was purchased from B-Braun (Melsungen, Germany). All reagents were of analytical grade. Colloids were prepared by a modified ethanol injection technique according to the following protocol:

0.5 ml of the aqueous solution of zoledronic acid 20 mg/ml in HEPES buffer 100 mM, pH 4.0, was mixed with 1 ml HEPES buffer 100 mM, pH 7.0 and transferred to 50 ml glass beaker. The beaker was put on a magnetic stirrer and the solution was stirred at 400 rpm using IKA big squid model stirrer (IKA, Königswinter Germany).

0.492 ml of a lipid solution in ethanol (DOTAP/DOPE; 2:1 molar ratio and total lipid concentration 180 and 90 mM for DOTAP and DOPE, respectively) was injected by a syringe (Syring type: Omnifix®-F 1 ml sterile plastic syringe, B. Braun; Melsungen, Germany, Needle: fine needle with 27G size) into the zoledronic acid solution under stirring.

After lipid injection, the suspension was stirred for 10 minutes.

After 10 minutes, 3 ml of RNAse free water were added to the colloid. The lipid and ZA dispersion was stirred for 20 minutes.

Filtration of the Colloid

The obtained raw dispersion of the colloidal dispersion was passed through a Minisart 0.45 µm CE membrane (Sartorius Stedim Biotech GmbH, Goettingen, Germany).

Dialysis of the Colloid

Dialysis of the filtered colloid to remove the free zoledronic acid and ethanol residue was carried out as follows:

Each 1 ml of the colloid was dialyzed versus 200 ml of PBS by using RNAses free Slide-A-Lyzer 10K Dialysis Cassettes (Thermo Fisher Scientific GmbH, Dreieich, Germany).

The dialysis took place at room temperature for 24 hr and at a stirring speed of 400 rpm. The colloid was recovered in sterile falcon tube for further physicochemical characterizations.

Retention of Zoledronic Acid (ZA) in the Colloid

Retained zoledronic acid was quantified by HPLC. The HPLC system consisted of a G1311B quaternary pump, a G4212B DAD (diode array detector) detector, a G1367E auto-sampler AS Hip, a G1330B column oven thermostat, and a ChemStation for LC revision B.04.02 (Agilent technologies, Colorado, USA). The stationary phase was xSelect CSH (C18) column (150 mm×4.6 mm×3.5 µm) (Waters, Eschborn, Germany). The mobile phase was a mixture of methanol (20%) and phosphate buffer 30 mM (80%) containing 5 mM tetrabutylammonium bromide (TCI Deutschland GmbH, Eschborn, Germany) adjusted to pH 7.2. An inoLab pH 7310P pH-meter (WTW, Weilheim, Germany) was used for pH determination of the mobile phase. The flow rate and the column oven temperature were 1 mL/min and 50° C. The detection wavelength was 215 nm. The injection volume amounted to 25 µl. Free zoledronic acid was determined by using high recovery Ultracel with a regenerated cellulose membrane and 30 KD MWCO (Millipore, Schwalbach/Ts., Germany) and using the following steps:

Removal of any preservatives by filtration of 0.1 M NaOH solution followed by PBS through the membrane.

Transfer of 500 µl of the colloid sample to 0.5 mL Ultracel tubes.

Centrifugation of the sample at 4000×g using 40° fixed angle rotor centrifuge Pico 21 (Thermoscientific, Osterode, Germany) at room temperature for 15 minutes.

Collection of the filtrate in a HPLC glass vial for quantification.

Measurement of zoledronic acid concentration in the filtrate by HPLC as mentioned above.

Retention Efficiency % Calculation

Retention efficiency %=[(Total ZA in dialyzed colloid−Free ZA in dialyzed colloid/Total ZA in dialyzed colloid]×(100).

Formation of LNPs Comprising ZA and RNA

According to the required ratio of cationic lipid/RNA (mole/base), the calculated volume of the ZA/lipid colloid was added to the calculated volume of RNA/PBS. The mixture incubated for at least 15 minutes to form LNPs.

Retention of Zoledronic Acid (ZA) as a Function of Starting ZA Concentration in Colloidal Lipid Dispersions The colloidal lipid dispersion was prepared by the ethanol injection technique as described above. Lipid composition was DOTMA/DOPE in a 2/1 molar ratio. ZA was dissolved in 100 mM HEPES buffer at concentration of 20 mg/ml and the pH adjusted to 4 approx. with 5M NaOH. The lipid concentration was approx. 12 mM. Retained and free zoledronic acid was quantified by HPLC. Free zoledronic acid was determined by using high recovery Ultracel with regenerated cellulose membrane and 30 KD MWCO. The samples were centrifuged at 4000×g using 40° fixed angle rotor centrifuge Pico 21 at room temperature for 15 minutes. The filtrate was collected in a HPLC vial for quantification.

Retention of ZA in LNPs Comprising Zoledronic Acid and RNA

Colloidal lipid dispersions comprising ZA with different molar fractions of lipid were mixed with PBS as a control, RNA, and Triton x100. The lipid composition was DOTMA/DOPE in a 2/1 molar ratio. ZA/lipid dispersions were prepared by mixing a calculated volume of lipid dispersions comprising ZA with the calculated volume of RNA at three different lipid concentrations 2, 4, and 6 mM. The ZA/lipid dispersions and RNA were mixed at 1:1 ratio (v/v). The cationic lipid/RNA charge ratio (mole/base) was 1:2. For PBS and Tritonx100, the calculated RNA volume was replaced by physiological PBS or Triton x100 aqueous solution of 10%. The LNPs comprising ZA and RNA were incubated for 30 minutes at room temperature. Afterwards, they were transferred to 0.5 mL Ultracel tubes previously cleaned from any preservatives by filtration of 0.1 M NaOH solution followed by PBS through the membrane. The samples were centrifuged at 4000×g using 40° fixed angle rotor centrifuge Pico 21 (Thermoscientific, Osterode, Germany) at room temperature for 15 minutes. The filtrate was collected in a HPLC glass vial for quantification. Measurement of zoledronic acid concentration in the filtrate by HPLC as mentioned above.

Example 6.3

1,2-dioleoyl-sn-glycero-3-ethylphosphocholine (DOEPC), 1,2-dioleoyl-sn-glycero-3-phosphocholine (DOPC) were purchased from Avanti Polar Lipids (Alabaster, Ala.). Cholesterol (purity 99%) was obtained from Sigma (St. Louis, Mo.). Zoledronic acid was obtained from CHEMOS GmbH (Regenstauf, Germany). RNAses free Phosphate buffer saline, hepes buffer were purchased from Ambion (Darmstadt, Germany). RNAse free water was purchased from B-Braun (Melsungen, Germany). All reagents were of analytical grade. Colloids were prepared by a modified ethanol injection technique according to the following protocol:

0.5 ml of the aqueous solution of zoledronic acid 20 mg/ml in HEPES buffer 100 mM, pH 4.0, was mixed with 1 ml HEPES buffer 100 mM, pH 7.0 and transferred to 50 ml glass beaker. The beaker was put on a magnetic stirrer and the solution was stirred at 400 rpm using IKA big squid model stirrer (IKA, Königswinter Germany).

0.492 ml of a lipid solution in ethanol (DOEPC/DOPC; 2:1 molar ratio and total lipid concentration 180 and 90 mM for DOEPC and DOPC, respectively) was injected by a syringe (Syring type: Omnifix®-F 1 ml sterile plastic syringe, B. Braun; Melsungen, Germany, Needle: fine needle with 27G size) into the zoledronic acid solution under stirring.

After lipid injection, the suspension was stirred for 10 minutes.

After 10 minutes, 3 ml of RNAse free water were added to the colloid. The lipid and ZA dispersion was stirred for 20 minutes.

ABBREVIATIONS

ZA=Zoledronic acid
LNPs=Lipid nanoparticles
Luc=Luciferase
infHA=influenza hemagglutinin A
IPP=Isopentenyl pyrophosphate
DOTMA=1,2-di-O-octadecenyl-3-trimethylammonium propane
DOPE=1,2-di-(9Z-octadecenoyl)-sn-glycero-3-phosphoethanolamine
DOTAP=1,2-dioleoyl-3-trimethylammonium-propane
DOEPC=1,2-dioleoyl-sn-glycero-3-ethylphosphocholine
i.v.=intra venous
DC=dentritic cell
iDC=immature dendritic cell
PBMCs=peripheral blood mononuclear cells
PBLs=peripheral blood lymphocytes
mΦ=macrophage
Cntr=control

The invention claimed is:

1. A method for delivering an antigen to antigen presenting cells in the spleen, or expressing an antigen in antigen presenting cells in the spleen, the method comprising administering to a subject a pharmaceutical composition comprising a lipid particle comprising:
   (i) 1,2-di-O-octadecenyl-3-trimethylammonium propane (DOTMA) and 1,2-di-(9Z-octadecenoyl)-sn-glycero-3-phosphoethanolamine (DOPE) in a 1:1 molar ratio,
   (ii) at least one water-soluble therapeutically effective compound for immunotherapy, and
   (iii) RNA encoding at least one antigen;
   wherein the pharmaceutical composition is administered intravenously, and wherein the RNA encoding at least one antigen is preferentially expressed in the spleen compared to the liver and lung.

2. The method of claim 1, wherein the therapeutically effective compound is a γδ T cell-stimulating bisphosphonate.

3. The method of claim 2 wherein the bisphosphonate is an aminobisphosphonate.

4. The method of claim 1, wherein RNA expression in the spleen is at least 5-fold the amount of RNA expression in the lung and/or liver.

5. The method of claim 3, wherein the aminobisphosphonate is zoledronic acid.

6. The method of claim 5, wherein the zoledronic acid concentration in the lipid particle is 0.05 µM to 50.0 µM.

7. The method of claim 1, wherein the RNA encoding at least one antigen encodes an antigen that is selected from the group consisting of a disease-associated antigen, a tumor antigen, a viral antigen, and a bacterial antigen.

8. The method of claim 1, wherein the number of positive charges derived from the lipid particle divided by the number of negative charges derived from the RNA is between 0.025 and 4.

* * * * *